(12) United States Patent
Sunagawa et al.

(10) Patent No.: US 11,219,395 B2
(45) Date of Patent: Jan. 11, 2022

(54) SLEEPINESS ESTIMATING DEVICE AND WAKEFULNESS INDUCING DEVICE

(71) Applicant: PANASONIC INTELLECTUAL PROPERTY MANAGEMENT CO., LTD., Osaka (JP)

(72) Inventors: Mika Sunagawa, Osaka (JP); Nawatt Silawan, Osaka (JP); Kunihiro Imamura, Osaka (JP); Shinichi Shikii, Nara (JP); Koichi Kusukame, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 12 days.

(21) Appl. No.: 16/630,363

(22) PCT Filed: Jun. 14, 2018

(86) PCT No.: PCT/JP2018/022652
§ 371 (c)(1),
(2) Date: Jan. 10, 2020

(87) PCT Pub. No.: WO2019/017124
PCT Pub. Date: Jan. 24, 2019

(65) Prior Publication Data
US 2020/0359954 A1    Nov. 19, 2020

(30) Foreign Application Priority Data
Jul. 19, 2017   (JP) .............................. JP2017-139715

(51) Int. Cl.
*A61B 5/18*   (2006.01)
*B60W 40/08*   (2012.01)
(Continued)

(52) U.S. Cl.
CPC ................ *A61B 5/18* (2013.01); *B60K 28/06* (2013.01); *B60W 40/08* (2013.01); *G06F 21/32* (2013.01); *G08B 21/06* (2013.01)

(58) Field of Classification Search
CPC . A61B 5/16; A61B 5/18; A61M 21/00; B60K 28/06; B60W 40/08; G06F 21/32; G08B 21/06
See application file for complete search history.

(56) References Cited

U.S. PATENT DOCUMENTS

| | | | | |
|---|---|---|---|---|
| 8,690,325 B1 * | 4/2014 | Straus | .................. | A61B 5/0002 351/200 |
| 2006/0094934 A1 | 5/2006 | Shirai et al. | | |

(Continued)

FOREIGN PATENT DOCUMENTS

| | | |
|---|---|---|
| JP | 2002-010995 A | 1/2002 |
| JP | 2005-318372 A | 11/2005 |

(Continued)

OTHER PUBLICATIONS

International Search Report and Written Opinion dated Sep. 11, 2018 in International Application No. PCT/JP2018/022652; with partial English translation.

*Primary Examiner* — Sisay Yacob
(74) *Attorney, Agent, or Firm* — McDermott Will and Emery LLP

(57) ABSTRACT

A sleepiness estimating device includes a biometric information acquirer that acquires biometric information of a person, an auxiliary information acquirer that acquires auxiliary information including at least one of five-sense information perceived by the person or emotion information indicating an emotion of the person, and a sleepiness estimator that estimates a sleepiness of the person based on the biometric information and the auxiliary information.

20 Claims, 17 Drawing Sheets

(51) Int. Cl.
  *B60K 28/06* (2006.01)
  *G08B 21/06* (2006.01)
  *G06F 21/32* (2013.01)

(56) References Cited

U.S. PATENT DOCUMENTS

| | | | |
|---|---|---|---|
| 2014/0125453 A1* | 5/2014 | McIntyre | H04L 63/107 |
| | | | 340/5.7 |
| 2015/0105976 A1 | 4/2015 | Shikii et al. | |
| 2016/0055689 A1* | 2/2016 | Raina | G07C 9/15 |
| | | | 340/5.7 |
| 2016/0055690 A1* | 2/2016 | Raina | G07C 9/28 |
| | | | 340/5.61 |
| 2016/0055693 A1* | 2/2016 | Somani | G07B 15/02 |
| | | | 340/5.61 |
| 2016/0055697 A1* | 2/2016 | Raina | G07C 9/00309 |
| | | | 340/5.7 |
| 2016/0163137 A1* | 6/2016 | Strulovitch | G07C 9/28 |
| | | | 340/5.61 |
| 2016/0374606 A1 | 12/2016 | Shikii et al. | |
| 2017/0020432 A1 | 1/2017 | Kusukame et al. | |
| 2017/0102765 A1* | 4/2017 | Yoneda | G06Q 30/0623 |
| 2017/0102783 A1 | 4/2017 | Shikii et al. | |
| 2017/0150930 A1 | 6/2017 | Shikii et al. | |
| 2018/0116579 A1* | 5/2018 | Omi | B60K 28/06 |

FOREIGN PATENT DOCUMENTS

| | | |
|---|---|---|
| JP | 2006-048171 A | 2/2006 |
| JP | 2006-115865 A | 5/2006 |
| JP | 2007-099249 A | 4/2007 |
| JP | 2007-264785 A | 10/2007 |
| JP | 2008-023127 A | 2/2008 |
| JP | 2010-133692 A | 6/2010 |
| JP | 2010-186276 A | 8/2010 |
| JP | 2015-018517 A | 1/2015 |
| JP | 2015-096413 A | 5/2015 |
| JP | 2017-012730 A | 1/2017 |
| JP | 2017-073107 A | 4/2017 |
| JP | 2017-099846 A | 6/2017 |
| JP | 2017-127616 A | 7/2017 |
| JP | 2019-006363 A | 1/2019 |

\* cited by examiner

FIG. 5

| AUXILIARY INFORMATION | SPECIFIC EXAMPLES |
|---|---|
| VISUAL INFORMATION | • CONTENT OF DISPLAYED MATERIAL (CATEGORY, ETC.)<br>• TEXT SIZE<br>• TEXT COLOR<br>• AMOUNT OF TEXT<br>• LUMINANCE INFORMATION OF DISPLAY<br>• COLOR INFORMATION OF DISPLAY |
| AUDITORY INFORMATION | • VOLUME OF SOUND<br>• TYPE OF SOUND (MUSIC, CONVERSATION, NOISE, ETC.)<br>• CONTENT OF SOUND (CATEGORY, ETC.)<br>• SOURCE OF SOUND (SPEAKER, ETC.) |
| OLFACTORY INFORMATION | • TYPE OF ODOR (RELAXING, IRRITANT ODOR, ETC.) |
| TASTE INFORMATION | • HISTORY INFORMATION OF MEALS<br>• FOOD BEING EATEN |
| TOUCH INFORMATION | • FREQUENCY AT WHICH SENSE OF TOUCH IS STIMULATED<br>• CHAIR INFORMATION |

FIG. 6

| AUXILIARY INFORMATION | LIKE CATEGORY | DISLIKE CATEGORY |
|---|---|---|
| VISUAL INFORMATION | • JAPANESE<br>• NOVEL<br>• SPORTS<br>• ACADEMIC SUBJECT (MATH, PHYSICS) | • ENGLISH<br>• THESIS<br>• NEWS<br>• ACADEMIC SUBJECT (LANGUAGE ARTS, HISTORY) |
| AUDITORY INFORMATION | • SMALL TALK | • WORK |

FIG. 7

| TIME | SUBJECT | CONTENT OF MEAL (ITEM PURCHASED) |
|---|---|---|
| 12:05 | USER A | ・RAMEN<br>・FRIED CHICKEN |
| 12:07 | USER B | ・STEAMED RISE<br>・MISO SOUP<br>・SALAD<br>・GRILLED FISH |
| 12:08 | USER C | ・SANDWICH<br>・COFFEE |
| ⋮ | ⋮ | ⋮ |

FIG. 8

| SLEEPINESS LEVEL | INTENSITY OF SLEEPINESS | FREQUENCY OF BLINKING |
|---|---|---|
| 1 | NOT SLEEPY | LOW ⇧ |
| 2 | ⋮ | |
| 3 | SLEEPY | |
| 4 | ⋮ | |
| 5 | VERY SLEEPY | ⇩ HIGH |

FIG. 9

| AUXILIARY INFORMATION | SLEEPINESS CAUSING DEGREE (HOW LIKELY PERSON BECOMES SLEEPY) ||
|---|---|---|
| | HIGH | LOW |
| VISUAL INFORMATION | ·DISLIKE CATEGORY<br>·TEXT SIZE: SMALL<br>·TEXT COLOR: BLACK AND WHITE<br>·AMOUNT OF TEXT: LARGE<br>·DISPLAY: DIM<br>·DISPLAY: BLACK AND WHITE | ·LIKE CATEGORY<br>·TEXT SIZE: LARGE<br>·TEXT COLOR: COLOR<br>·AMOUNT OF TEXT: SMALL<br>·DISPLAY: BRIGHT<br>·DISPLAY: COLOR |
| AUDITORY INFORMATION | ·VOLUME OF SOUND: SMALL<br>·DISLIKE CATEGORY<br>·MUSIC: SLOW TEMPO<br>·SPEAKER: PERSON WHOM USER DOES NOT GET ALONG<br>·CONVERSATION: MONOTONOUS | ·VOLUME OF SOUND: LARGE<br>·LIKE CATEGORY<br>·MUSIC: UP-TEMPO<br>·SPEAKER: PERSON WHOM USER LIKES<br>·CONVERSATION: LIVELY |
| OLFACTORY INFORMATION | ·RELAXING | ·IRRITANT ODOR |
| TASTE INFORMATION | ·AMOUNT OF MEAL: LARGE<br>·SOMETHING SWEET TO EAT | ·AMOUNT OF MEAL: SMALL<br>·MEAL CONTAINING CAFFEINE |
| TOUCH INFORMATION | ·FREQUENCY OF STIMULUS: LOW<br>·SOFT CHAIR | ·FREQUENCY OF STIMULUS: HIGH<br>·HARD CHAIR |

FIG. 10

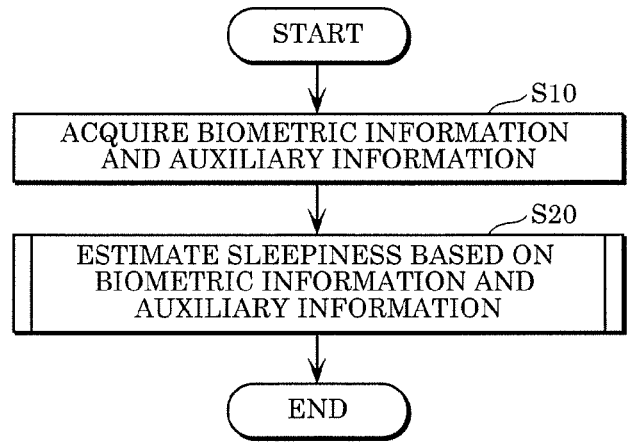

FIG. 16
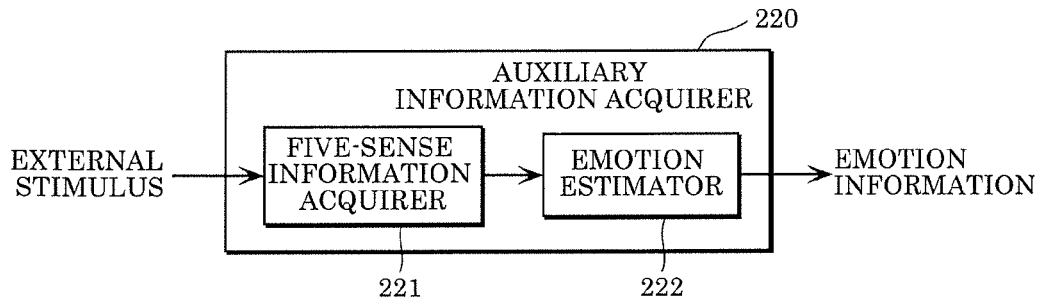
FIG. 17
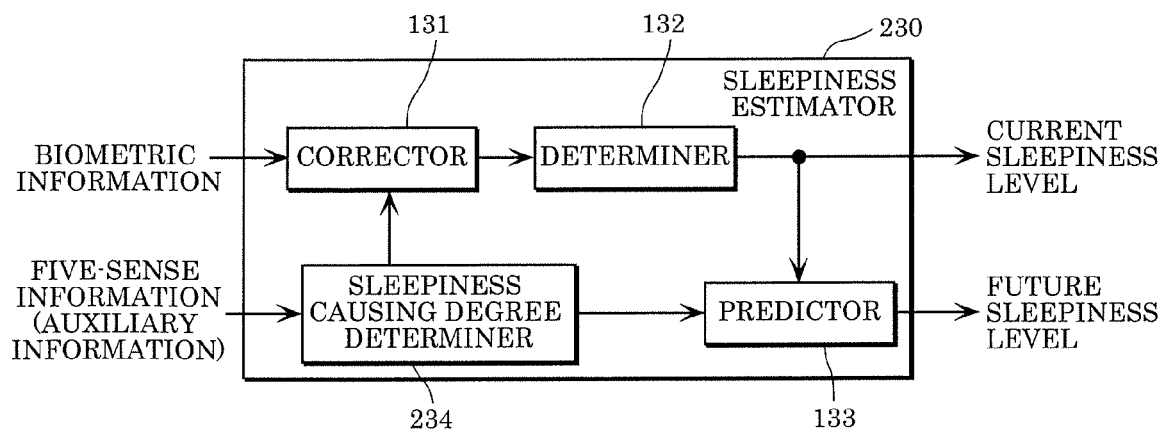
FIG. 18
| AUXILIARY INFORMATION | SLEEPINESS CAUSING DEGREE (HOW LIKELY PERSON BECOMES SLEEPY) | |
|---|---|---|
| | HIGH | LOW |
| EMOTION INFORMATION | ·MILD EMOTION<br>·PLEASANT EMOTION | ·INTENSE EMOTION<br>·UNPLEASANT EMOTION |

FIG. 34
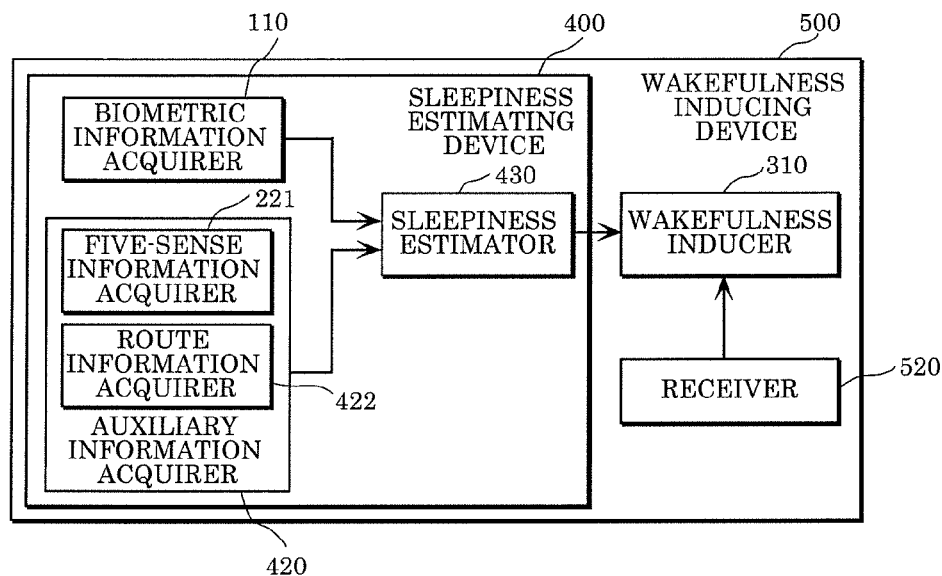
FIG. 35
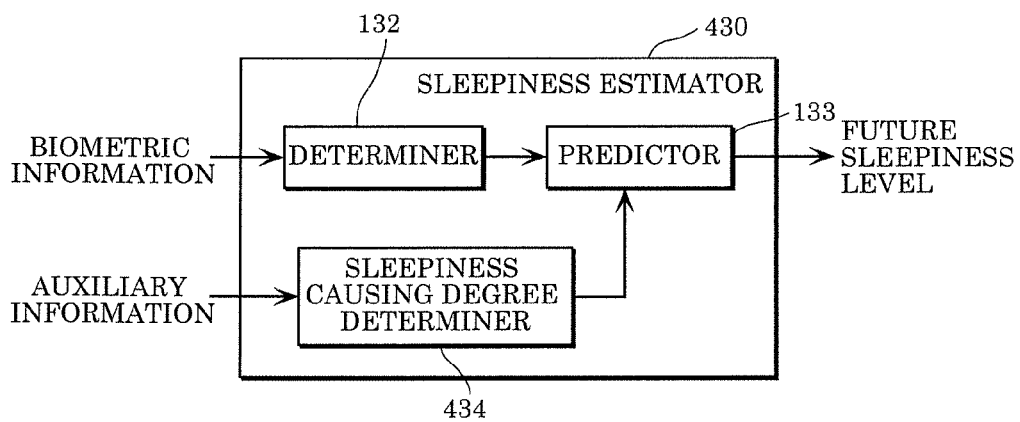
FIG. 36
| ROAD | DETAILED INFORMATION | | | |
|---|---|---|---|---|
| | AUTONOMOUS DRIVING | STREETLIGHT | TRAFFIC VOLUME | OTHER |
| A004 | NOT ALLOWED | NORMAL | NORMAL | ACCIDENT-PRONE |
| B003 | ALLOWED | MANY | HEAVY | — |
| A001 | ALLOWED | MANY | NORMAL | — |
| B001 | NOT ALLOWED | NORMAL | LIGHT | SCHOOL ZONE |
| A002 | NOT ALLOWED | FEW | LIGHT | SCHOOL ZONE |

FIG. 37

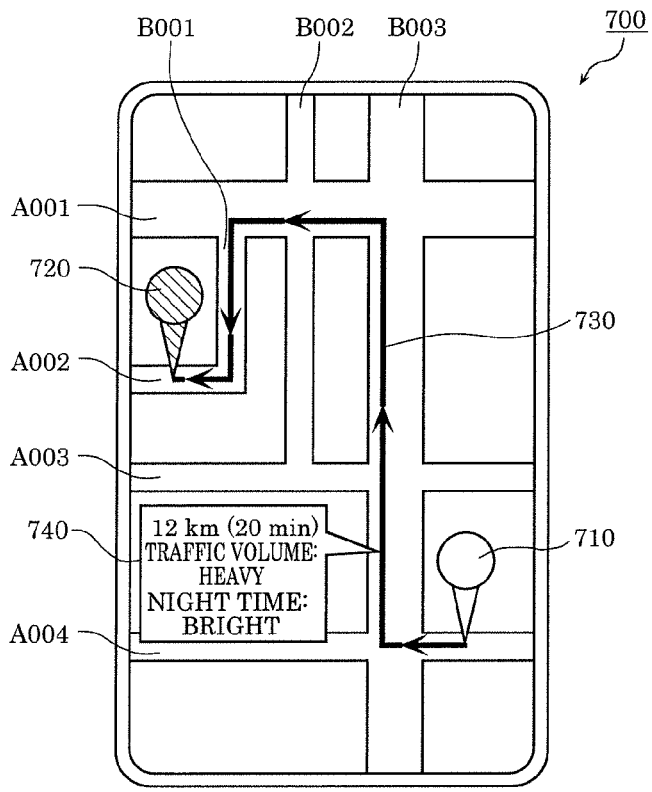

FIG. 38

| ROUTE INFORMATION | SLEEPINESS CAUSING DEGREE (HOW LIKELY PERSON BECOMES SLEEPY) = WAKING STIMULUS | |
|---|---|---|
| | HIGH | LOW |
| DISTANCE | LONG | SHORT |
| DRIVING TIME | LONG | SHORT |
| TRAFFIC VOLUME | HEAVY | LIGHT |
| BRIGHTNESS ON ROAD (NUMBER OF STREETLIGHTS) | DARK (SMALL) | BRIGHT (LARGE) |
| AUTONOMOUS DRIVING | IMMEDIATELY BEFORE END OF AUTONOMOUS DRIVING | IMMEDIATELY AFTER START OF AUTONOMOUS DRIVING |
| OTHER | ACCIDENT-PRONE SCHOOL ZONE LONG TUNNEL | |

SLEEPINESS ESTIMATING DEVICE AND WAKEFULNESS INDUCING DEVICE

CROSS-REFERENCE OF RELATED APPLICATIONS

This application is the U.S. National Phase under 35 U.S.C. § 371 of International Patent Application No. PCT/JP2018/022652, filed on Jun. 14, 2018, which in turn claims the benefit of Japanese Application No. 2017-139715, filed on Jul. 19, 2017, the entire disclosures of which Applications are incorporated by reference herein.

TECHNICAL FIELD

The present disclosure relates to a sleepiness estimating device and a wakefulness inducing device.

BACKGROUND ART

To date, there are studies on how to estimate a person's sleepiness with use of his/her biometric information. For example, PTL 1 discloses a sleepiness detecting device that extracts, based on an image obtained by capturing an image of a user's face, a feature amount of a change in the face and detects the sleepiness of the user based on the extracted feature amount.

CITATION LIST

Patent Literature

PTL 1: Japanese Unexamined Patent Application Publication No. 2007-264785

SUMMARY OF THE INVENTION

Technical Problem

The existing sleepiness detecting device described above, however, suffers from shortcomings in that the accuracy of estimating the sleepiness is not sufficient.

Accordingly, the present disclosure provides a sleepiness estimating device and a wakefulness inducing device that can estimate the sleepiness with high accuracy.

Solutions to Problem

To address the shortcomings described above, a sleepiness estimating device according to one aspect of the present disclosure includes a biometric information acquirer that acquires biometric information of a person, an auxiliary information acquirer that acquires auxiliary information including at least one of five-sense information perceived by the person or emotion information indicating an emotion of the person, and a sleepiness estimator that estimates a sleepiness of the person based on the biometric information and the auxiliary information.

A wakefulness inducing device according to one aspect of the present disclosure includes the above sleepiness estimating device and a wakefulness inducer that induces wakefulness in the person based on the sleepiness estimated by the sleepiness estimator.

Advantageous Effect of Invention

The present disclosure allows the sleepiness to be estimated with high accuracy.

BRIEF DESCRIPTION OF DRAWINGS

FIG. 5 illustrates an example of auxiliary information (five-sense information) according to Embodiment 1.

FIG. 6 illustrates an example of a like category and a dislike category of a user.

FIG. 7 illustrates an example of meal history information.

FIG. 8 illustrates an example of a relationship among the sleepiness level, the intensity of sleepiness, and the frequency of blinking, which is an example of biometric information.

FIG. 9 illustrates an example of a relationship between auxiliary information (five-sense information) and a sleepiness causing degree (how likely a person becomes sleepy).

FIG. 10 is a flowchart illustrating an operation of the sleepiness estimating device according to Embodiment 1.

FIG. 16 is a block diagram illustrating a functional configuration of an auxiliary information acquirer of the sleepiness estimating device according to Embodiment 2.

FIG. 17 is a block diagram illustrating a functional configuration of a sleepiness estimator of the sleepiness estimating device according to Embodiment 2.

FIG. 18 illustrates an example of a relationship between auxiliary information (emotion information) and a sleepiness causing degree (how likely a person becomes sleepy).

FIG. 34 is a block diagram illustrating a functional configuration of the wakefulness inducing device according to Embodiment 4.

FIG. 35 is a block diagram illustrating a functional configuration of a sleepiness estimator of a sleepiness estimating device according to Embodiment 4.

FIG. 36 illustrates route information to be acquired by the sleepiness estimating device according to Embodiment 4.

FIG. 37 illustrates a map including the route information illustrated in FIG. 36.

FIG. 38 illustrates an example of a relationship between auxiliary information (route information) and a sleepiness causing degree (how likely a person becomes sleepy) or the intensity of a waking stimulus.

Figure 1:
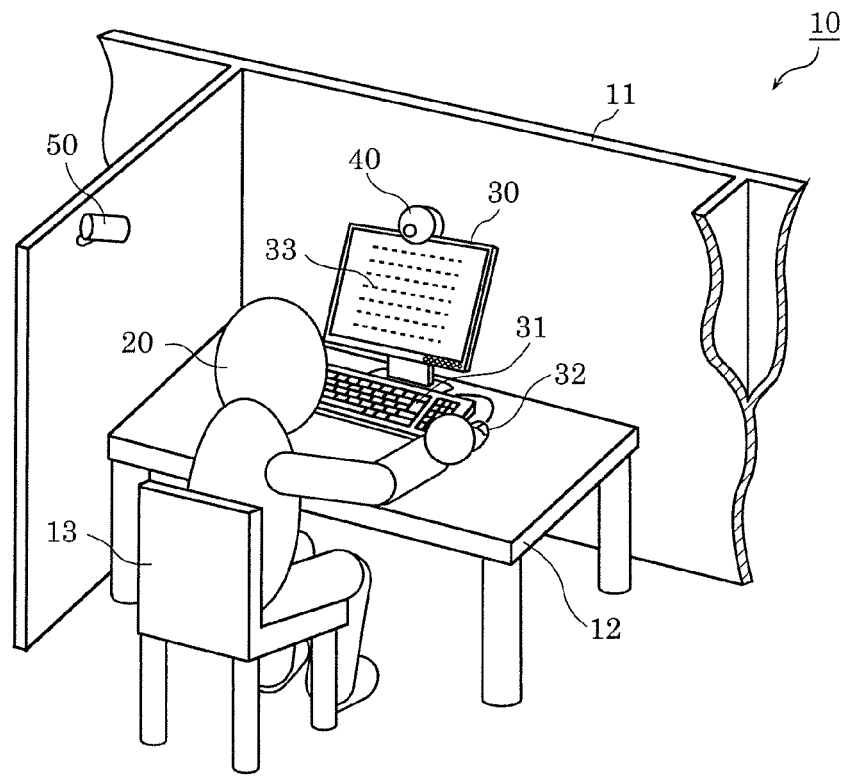
FIG. 1 illustrates an application example of a sleepiness estimating device according to Embodiment 1.

DESCRIPTION OF EXEMPLARY EMBODIMENTS (Overview of the Present Disclosure)

To address the shortcomings described above, a sleepiness estimating device according to one aspect of the present disclosure includes a biometric information acquirer that acquires biometric information of a person, an auxiliary information acquirer that acquires auxiliary information including at least one of five-sense information perceived by the person or emotion information indicating an emotion of the person, and a sleepiness estimator that estimates a sleepiness of the person based on the biometric information and the auxiliary information.

This configuration makes it possible to estimate the sleepiness with high accuracy since not only the biometric information but also the auxiliary information is used.

For example, the sleepiness estimator may include a corrector that corrects the biometric information based on the auxiliary information, and a determiner that determines the sleepiness of the person based on the biometric information corrected by the corrector.

This configuration makes it possible to estimate the sleepiness with high accuracy since corrected biometric information is used.

For example, the sleepiness estimator may include a determiner that determines the sleepiness of the person at a first point in time based on the biometric information, and a predictor that predicts the sleepiness of the person at a second point in time that is after the first point in time based on the auxiliary information and the sleepiness determined by the determiner.

This configuration makes it possible to estimate a future sleepiness with high accuracy.

For example, the five-sense information may include visual information on a stimulus for sight of the person.

Since, among the five-sense information, the visual information includes a prominently large amount of information, the use of the visual information makes it possible to estimate the sleepiness with higher accuracy.

For example, the auxiliary information acquirer may acquire, as the visual information, a content of a displayed material at which the person is looking.

The content of the displayed material includes a category of the displayed material, the text size or the amount of text, or the brightness of the displayed material, for example. The content of the displayed material has a large influence on the sleepiness of a person. For example, when the text size is small or when the amount of text is large, the sleepiness is more likely to be induced. Therefore, the use of the content of the displayed material as the visual information makes it possible to estimate the sleepiness with higher accuracy.

For example, the sleepiness estimator may include a learner that learns a preference of the person regarding the displayed material, and estimate the sleepiness of the person based further on a learning result of the learner.

The preference regarding the displayed material has a large influence on the sleepiness. For example, the sleepiness is suppressed when a person is looking at his/her favorite content, and the sleepiness is induced when a person is looking at the content that he/she does not like. Therefore, learning the preference regarding the content through machine learning makes it possible to estimate the sleepiness with higher accuracy.

For example, the sleepiness estimator may estimate the sleepiness of the person based further on a manner of operation performed by the person on the displayed material.

For example, it can be estimated that, when a person operates the displayed material more frequently, his/her sleepiness is suppressed and the person is more focused on operating the displayed material and that, when the person operates the displayed material less frequently, his/her sleepiness becomes higher. In this manner, the use of information on the manner of operation on the displayed material makes it possible to estimate the sleepiness with higher accuracy.

For example, the five-sense information may include auditory information on a stimulus for hearing of the person.

The use of the auditory information makes it possible to estimate the sleepiness with high accuracy.

For example, the auxiliary information acquirer may acquire, as the auditory information, audio information in surroundings of the person.

When the volume of a sound present in the surroundings of a person is large, the sound is more likely to induce wakefulness in the person, for example. Thus, such a sound has a large influence on the sleepiness of a person. Therefore, acquiring the audio information of the surroundings of a person as the auditory information makes it possible to estimate the sleepiness with high accuracy.

For example, the five-sense information may include olfactory information on a stimulus for a sense of smell of the person.

Since there is an odor that induces a relaxation effect or a waking effect, the use of the olfactory information makes it possible to estimate the sleepiness with high accuracy.

For example, the five-sense information may include taste information on a stimulates for taste of the person.

Upon having a meal, a person may become sleepy due to a change in the blood sugar level, the feeling of fullness, and so on. Therefore, the use of the taste information makes it possible to estimate the sleepiness with high accuracy.

For example, the auxiliary information acquirer may acquire, as the taste information, meal history information of the person.

Grasping the food eaten by the person makes it possible to estimate the sleepiness with high accuracy.

For example, the auxiliary information acquirer may acquire, as the taste information, information indicating food that the person is eating.

Grasping the food eaten by the person makes it possible to estimate the sleepiness with high accuracy.

For example, the five-sense information may include touch information on a stimulus for a sense of touch of the person.

The use of the touch information makes it possible to estimate the sleepiness with high accuracy.

For example, the auxiliary information acquirer may acquire, as the touch information, a frequency at which the sense of touch of the person is stimulated.

For example, when a person is doing some work, the sense of touch of the person is stimulated in accordance with the work the person is doing (e.g., an input through a keyboard). Therefore, the use of the frequency at which the sense of touch is stimulated as the touch information makes it possible to estimate the sleepiness with high accuracy.

For example, the auxiliary information acquirer may acquire, as the touch information, information on a chair on which the person is sitting.

For example, the sleepiness is less likely to be induced when the chair is hard, and the sleepiness is more likely to be induced when the chair is soft. Therefore, the use of chair information makes it possible to estimate the sleepiness with high accuracy.

For example, the biometric information acquirer may acquire, as the biometric information, information on blinking of the person.

A person blinks more frequently when he/she is sleepy, and a person blinks less frequently when he/she is not sleepy. Alternatively, the cycle of blinking becomes unstable when a person is sleepy, and the cycle of blinking is stable when a person is not sleepy. In this manner, the behavior of blinking correlates with the sleepiness of a person. Therefore, the use of the information on blinking as the biometric information makes it possible to estimate the sleepiness with high accuracy.

A wakefulness inducing device according to one aspect of the present disclosure may include the above sleepiness estimating device and a wakefulness inducer that induces wakefulness in the person based on the sleepiness estimated by the sleepiness estimator.

This configuration makes it possible to induce wakefulness in a person based on the sleepiness estimated with high accuracy and thus to shake off the person's sleepiness with high efficiency. Therefore, the amount of energy consumed to induce wakefulness can be reduced, the power consumption can be reduced, and the energy can be saved, for example.

For example, the wakefulness inducer may change an image displayed on a display of an electronic device operated by the person.

A change in the image displayed on the display can stimulate a person with a high sleepiness level. For example, making the person restore the changed image to the original image can further shake off the person's sleepiness.

For example, the wakefulness inducer may communicate information on the sleepiness of the person.

As the information on the sleepiness is communicated to his/her surroundings, another person, or the like, the sense of shame can be induced in the person. This not only shakes off the sleepiness that the person has when he/she is prompted to be wakeful but also helps keep the person stay tense in the future, and this can keep the sleepiness from being induced.

Hereinafter, some embodiments will be described in concrete terms with reference to the drawings.

The embodiments described below merely illustrate general or specific examples. The numerical values, the shapes, the materials, the components, the arrangement positions and the connection modes of the components, the steps, the order of the steps, and so on illustrated in the following embodiments are examples and are not intended to limit the present disclosure. Among the components in the following embodiments, any component that is not in an independent claim expressing the broadest concept is to be regarded as an optional component.

The drawings are schematic diagrams and do not necessarily provide the exact depictions. Therefore, the scales and so on do not necessarily match among the drawings, for example. In the drawings, substantially identical configurations are given identical reference characters, and duplicate descriptions thereof will be omitted or simplified.

Embodiment 1

[1-1. Overview]

First, an overview of a sleepiness estimating device according to Embodiment 1 will be described with reference to FIG. 1. FIG. 1 illustrates an application example of a sleepiness estimating device according to Embodiment 1.

Sleepiness estimating device 100 (see FIG. 2) according to the present embodiment is applied to office environment 10, such as the one illustrated in FIG. 1, and estimates the sleepiness of user 20. Sleepiness estimating device 100 estimates the sleepiness of user 20 based on biometric information of user 20 and five-sense information perceived by user 20.

As illustrated in FIG. 1, office environment 10 includes a plurality of individual spaces that are divided by partition board (partition) 11, for example. Desk 12 and chair 13 are disposed in each individual space. User 20 is sitting on chair 13 and performs an intellectual operation, such as work, at desk 12.

In the example illustrated in FIG. 1, display 30, keyboard 31, and mouse 32 are disposed on desk 12. For example, user 20 creates and edits a document by operating keyboard 31 and mouse 32 while looking at displayed material 33, such as a text, displayed on display 30.

In the present embodiment, as illustrated in FIG. 1, camera 40 for capturing an image of user 20 is attached to display 30. Camera 40 is an example of an information acquiring device (sensing device) for acquiring biometric information of user 20. There is no particular limitation on the position where camera 40 is attached, and camera 40 may be attached to desk 12, partition board 11, an interior wall, a ceiling, or the like.

Furthermore, as illustrated in FIG. 1, camera 50 for capturing an image of displayed material 33 is attached to partition board 11. Camera 50 is an example of an information acquiring device (sensing device) for acquiring visual information, which is an example of five-sense information. There is no particular limitation on the position where camera 50 is attached, and camera 50 may be attached to desk 12. Camera 40 and camera 50 may be served by a single camera.

Although office environment 10 is illustrated as an example in FIG. 1, sleepiness estimating device 100 can be applied to an environment other than office environment 10. For example, sleepiness estimating device 100 may be applied to an environment, such as a school or an after-school learning center, where students study and may estimate the sleepiness of a learner, such as a student.

Alternatively, sleepiness estimating device 100 may be applied to an moving body, such as an automobile, a train, or an aircraft, and may estimate the sleepiness of a driver, a pilot, or the like.

[1-2. Configuration]

Now, with reference to FIGS. 2 to 4, a configuration of sleepiness estimating device 100 according to the present embodiment will be described.

Figure 2:
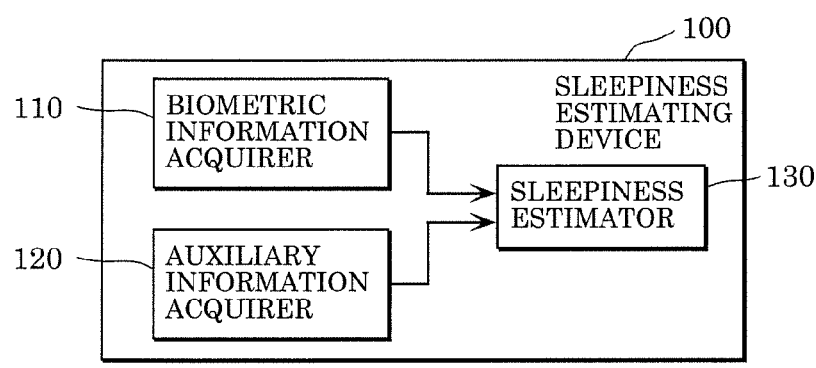
FIG. 2 is a block diagram illustrating a functional configuration of the sleepiness estimating device according to Embodiment 1.

FIG. 2 is a block diagram illustrating a functional configuration of sleepiness estimating device 100 according to the present embodiment. FIG. 3 is a block diagram illustrating a functional configuration of auxiliary information acquirer 120 of sleepiness estimating device 100 according to the present embodiment. FIG. 4 is a block diagram illustrating a functional configuration of sleepiness estimator 130 of sleepiness estimating device 100 according to the present embodiment.

As illustrated in FIG. 2, sleepiness estimating device 100 includes biometric information acquirer 110, auxiliary information acquirer 120, and sleepiness estimator 130.

[1-2-1. Biometric Information Acquirer]

Biometric information acquirer 110 acquires biometric information of a person. In the present embodiment, biometric information acquirer 110 acquires, as biometric information, information on blinking of a person. Information on blinking of a person includes, for example, the cycle of blinking and the frequency of blinking.

Biometric information is not limited to information on blinking of a person and may be any piece of physiological information manifested by a person. For example, biometric information may be information on an amount of change in the line of sight. Alternatively, biometric information may be information on yawning, such as the frequency of yawning. Biometric information may be information on breathing, pulsation, heartbeat, a blood pressure, a body temperature, a skin temperature, or the like.

In the present embodiment, biometric information acquirer 110 is implemented by camera 40 illustrated in FIG. 1, a processor (not illustrated), and so on, for example. Specifically, biometric information acquirer 110 acquires biometric information based on a captured image obtained as camera 40 captures an image of user 20. A captured image is, for example, a moving image (video) but may instead be a still image.

Biometric information acquirer 110 performs image processing, such as edge detection, on a captured image to extract the eyes of user 20 and acquires the number of times user 20 blinks per predetermined period (i.e., the frequency of blinking) as biometric information. In addition, biometric information acquirer 110 may extract the mouth of user 20 from a captured image and acquire the number of times user 20 yawns per predetermined period (i.e., the frequency of yawning) as biometric information.

Depending on the type of biometric information to be acquired, biometric information acquirer 110 may be implemented by hardware other than camera 40. For example, biometric information acquirer 110 may be implemented by a microphone and acquire a sound produced when user 20 yawns. Furthermore, biometric information acquirer 110 may be implemented by an electrode, a sensor, or the like to be attached to user 20 and acquire his/her breathing, pulsation, heartbeat, blood pressure, body temperature, skin temperature, or the like. Biometric information acquirer 110 may also be implemented by an infrared sensor, a thermal image sensor, or the like.

[1-2-2. Auxiliary Information Acquirer]

Auxiliary information acquirer 120 acquires five-sense information perceived by a person as auxiliary information. Specifically, five-sense information is stimulus information on a stimulus for the senses of a person. In the present embodiment, the senses of a person include at least one of sight, hearing, smell, taste, or touch. Therefore, as illustrated in FIG. 5, auxiliary information (specifically, five-sense information) includes at least one of visual information, auditory information, olfactory information, taste information, or touch information. FIG. 5 illustrates an example of auxiliary information (five-sense information) according to the present embodiment.

Figure 3:
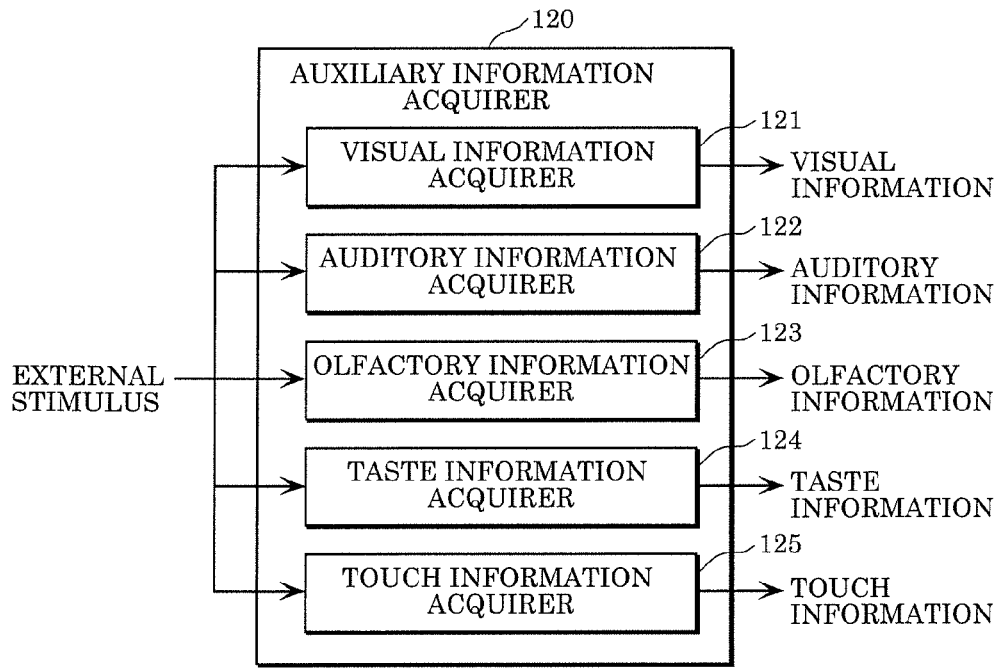
FIG. 3 is a block diagram illustrating a functional configuration of an auxiliary information acquirer of the sleepiness estimating device according to Embodiment 1.

In the present embodiment, as illustrated in FIG. 3, auxiliary information acquirer 120 includes visual information acquirer 121, auditory information acquirer 122, olfactory information acquirer 123, taste information acquirer 124, and touch information acquirer 125. It suffices that auxiliary information acquirer 120 include at least one of visual information acquirer 121, auditory information acquirer 122, olfactory information acquirer 123, taste information acquirer 124, or touch information acquirer 125, and auxiliary information acquirer 120 may lack one of more of the above. For example, auxiliary information acquirer 120 may include only visual information acquirer 121.

[1-2-2-1. Visual Information Acquirer]

Visual information acquirer 121 acquires visual information on a stimulus for the sight of a person. Visual information acquirer 121 is implemented by camera 50 illustrated in FIG. 1, a processor (not illustrated), and so on, for example. In the present embodiment, visual information acquirer 121 acquires, as visual information, information on light that enters the eyes of user 20. Specifically, visual information acquirer 121 acquires, as visual information, the content of displayed material 33 at which user 20 is looking based on a captured image obtained as camera 50 captures an image of displayed material 33.

For example, when displayed material 33 includes a text, as illustrated in FIG. 5, visual information may include the text size, the text color, and the amount of text of displayed material 33. Visual information may further include luminance information (brightness) and color information of display 30.

In the present embodiment, displayed material 33 is an image displayed on display 30. Specifically, displayed material 33 is an image representing a document or the like that user 20 is creating or editing. Displayed material 33 is, for example, a still image but may instead be a moving image.

Displayed material 33 may display only a text or may display a text with a figure, a design, or the like. Alternatively, displayed material 33 may display only a figure or a design. Displayed material 33 does not need to be an image displayed on display 30. For example, displayed material 33 may be a printed material, such as a book or a newspaper.

Displayed material 33 is categorized into one of a plurality of categories in accordance with its content. The plurality of categories are defined in advance in accordance with an environment to which user 20 belongs. For example, when user 20 works in office environment 10, the plurality of categories include categories corresponding to the language of displayed material 33, such as "English document" and "Japanese document". The plurality of categories further include categories corresponding to the content, such as "proposal", "news", and "sports". When user 20 belongs to a learning environment, the plurality of categories may include categories corresponding to the subjects, such as "math", "physics", "language arts", and "history". When user 20 belongs to a reading environment, the plurality of categories may include categories corresponding to genres, such as "novel" and "thesis".

The plurality of categories can each be categorized into a like category that user 20 likes and a dislike category that user 20 does not like. FIG. 6 illustrates an example of the like category and the dislike category of user 20. FIG. 6 illustrates an example in which the categories in visual information and auditory information are categorized, but this is not a limiting example. Each category in at least one of olfactory information, taste information, or touch information may also be categorized into a like category or a dislike category in a similar manner.

In the example illustrated in FIG. 6, the like category of user 20 includes content displayed in "Japanese", "novel", "sports", and the academic subjects "math" and "physics". The dislike category of user 20 includes content displayed in "English", "thesis", "news", and the academic subjects "language arts" and "history".

Whether displayed material 33 is categorized into a like category or a dislike category is defined in advance by user 20, and this information is stored in a memory (not illustrated) or the like as category information. Alternatively, as in Variation 1 described later, category information may be generated through machine learning or the like.

Visual information acquirer 121 may be implemented by hardware other than camera 50. For example, when displayed material 33 is an image displayed on display 30, visual information acquirer 121 may acquire image information that a computer (not illustrated) outputs to display 30. Specifically, visual information acquirer 121 may be a communication interface (IF) connected to a computer. In other words, visual information acquirer 121 may directly acquire image data or video data.

The communication IF is, for example, a connector to be connected to a cable or the like for wired communication, a wireless communication module, or the like. The communication IF carries out wired communication or wireless communication with a device on the connection end, such as a computer.

[1-2-2-2. Auditory Information Acquirer]

Auditory information acquirer 122 acquires auditory information on a stimulus for the hearing of a person. Auditory information acquirer 122 is implemented by a microphone, a processor (not illustrated), and so on, for example. In the present embodiment, auditory information acquirer 122 acquires, as auditory information, audio information on the surroundings of user 20. Specifically, auditory information acquirer 122 acquires auditory information based on audio data obtained as a microphone collects a sound in the surroundings of user 20. As illustrated in FIG. 5, auditory information includes the volume of a sound, the type of a sound, the content of a sound, the source of a sound, and so on.

In the present embodiment, as with displayed material 33, an acquired sound is categorized into one of a plurality of categories in accordance with its content. The plurality of categories can each be categorized into a like category or a dislike category. For example, in the example illustrated in FIG. 6, the like category includes "small talk", and the dislike category includes "work".

Auditory information acquirer 122 may be implemented by hardware other than the microphone. For example, when a speaker is disposed in the surroundings of user 20 and the speaker outputs a sound, auditory information acquirer 122 may acquire audio data that a computer outputs to the speaker. Specifically, auditory information acquirer 122 may be a communication IF connected to the speaker. The speaker is, for example, a speaker of AV equipment, such as display 30 or a music player of user 20, a speaker attached to, for example, the ceiling, or the like.

[1-2-2-3. Olfactory Information Acquirer]

Olfactory information acquirer 123 acquires olfactory information on a stimulus for the sense of smell of a person. Olfactory information acquirer 123 is implemented by an odor sensor (gas sensor), a processor (not illustrated), and so on, for example. In the present embodiment, olfactory information acquirer 123 acquires, as olfactory information, information on an odor in the surroundings of user 20. Specifically, the odor sensor detects an odor in the surroundings of user 20, and olfactory information acquirer 123 acquires olfactory information based on a detected odor component. As illustrated in FIG. 5, olfactory information includes the type of an odor.

Olfactory information acquirer 123 may be implemented by hardware other than the odor sensor. For example, when a scent-emitting device, such as an aroma diffuser, that emits a scent (odor) is disposed in the surroundings of user 20 and a scent (odor) is emitted from the scent-emitting device, olfactory information acquirer 123 may acquire a setting value of the scent-emitting device. Specifically, olfactory information acquirer 123 may be a communication IF connected to the scent-emitting device.

[1-2-2-4. Taste Information Acquirer]

Taste information acquirer 124 acquires taste information on a stimulus for the taste of a person. Taste information acquirer 124 is implemented by a camera, a processor (not illustrated), and so on, for example. In the present embodiment, taste information acquirer 124 acquires, as taste information, food information indicating what user 20 is eating. Specifically, taste information acquirer 124 acquires food information based on a captured image obtained as the camera captures an image of the surroundings of user 20. The camera may be at least one of camera 40 or camera 50 illustrated in FIG. 1. For example, the camera may capture an image of a top surface of desk 12 to capture an image of a package or the like for the food placed on desk 12. Alternatively, the camera may capture an image of a mouth area of user 20 to capture an image of the food that user 20 is eating.

Taste information acquirer 124 may be implemented by hardware other than the camera. For example, taste information acquirer 124 may be implemented by a microphone and acquire a sound uttered by user 20 regarding what user 20 is eating.

Alternatively, taste information acquirer 124 may be implemented by a communication IF that communicates with a management server at a company cafeteria or store. For example, taste information acquirer 124 may acquire, as taste information, meal history information of a person. The meal history information is, for example, information managed by the management server at the company cafeteria or store and corresponds to the record of foods that user 20 has purchased.

FIG. 7 illustrates an example of meal history information. As illustrated in FIG. 7, the purchase time, the subject (user), and the content of each meal (content of each purchase) are associated with each other and stored as history information. Managing the purchase history of each of a plurality of users 20 in this manner makes it easier to manage the meal history information of each user.

For example, for his/her own health maintenance, user 20 may install a health maintenance application in a mobile information terminal, such as a smartphone, of user 20 and input the content or the like of each meal. Taste information acquirer 124 may cooperate with such a health maintenance application and acquire the input content of each meal as history information.

[1-2-2-5. Touch Information Acquirer]

Touch information acquirer 125 acquires touch information on a stimulus for the sense of touch of a person. Touch information acquirer 125 is implemented by a seat sensor attached to chair 13, a processor (not illustrated), and so on, for example. In the present embodiment, the seat sensor detects a contact with user 20, and based on the detection result, touch information acquirer 125 acquires touch information.

In the present embodiment, touch information is information on the frequency at which the sense of touch of a person has been stimulated. For example, touch information acquirer 125 acquires, as touch information, the frequency at which user 20 repositions himself/herself on chair 13.

Touch information acquirer 125 may be implemented by hardware other than the seat sensor. For example, touch information acquirer 125 may be implemented by a camera, and as the camera captures an image of user 20, touch information acquirer 125 may acquire, as touch information, the frequency at which user 20 repositions himself/herself.

Alternatively, touch information acquirer 125 may be implemented by keyboard 31, mouse 32, or the like and may acquire the frequency of its operation by user 20 as touch information. For example, touch information acquirer 125 may acquire, as touch information, at least one of the number of times keys on keyboard 31 are hit per unit time or the number of times mouse 32 is clicked per unit time.

Alternatively, touch information acquirer 125 may acquire, as touch information, chair information on chair 13 on which user 20 is sitting. Chair information is information indicating the material or the like of chair 13, for example. Chair information is registered in advance by user 20, a manager, or the like and stored in a memory or the like included in sleepiness estimating device 100. Touch information acquirer 125 may retrieve chair information from the memory to acquire the chair information.

[1-2-3. Sleepiness Estimator]

Sleepiness estimator 130 estimates the sleepiness of a person based on biometric information and auxiliary information. In the present embodiment, sleepiness estimator 130 estimates the current sleepiness and the future sleepiness of a person based on biometric information and auxiliary information. Specifically, as illustrated in FIG. 4, sleepiness estimator 130 includes corrector 131, determiner 132, predictor 133, and sleepiness causing degree determiner 134.

Sleepiness estimator 130 is implemented by a non-volatile memory storing a program, a volatile memory serving as a temporary storage area for executing a program, an input/output port, a processor that executes a program, and so on, for example.

The current sleepiness is an example of the sleepiness of user 20 held at a first point in time. For example, the current sleepiness is the sleepiness held at a point when biometric information acquirer 110 has acquired biometric information or when auxiliary information acquirer 120 has acquired auxiliary information. The future sleepiness is an example of the sleepiness held at a second point in time that is after the first point in time and is the sleepiness of user 20 to be held when a predetermined duration will have passed after the first point in time. The predetermined duration is, for example, 10 minutes, 30 minutes, 1 hour, or the like, and there is no particular limitation on the predetermined duration.

In the present embodiment, the sleepiness of a person is expressed by a plurality of sleepiness levels. FIG. 8 illustrates an example of a relationship among the sleepiness level, the intensity of sleepiness, and the frequency of blinking, which is an example of biometric information. For example, as illustrated in FIG. 8, the sleepiness level is expressed in five levels—from "1" to "5". A lower sleepiness level indicates that the person is less sleepy, and a higher sleepiness level indicates that the person is more sleepy. The method of expressing the sleepiness is not limited to the example illustrated in FIG. 8. For example, the sleepiness may be expressed in two levels—"sleepy" and "not sleepy".

[1-2-3-1. Corrector]

Corrector 131 corrects biometric information based on auxiliary information. In the present embodiment, corrector 131 corrects biometric information based on a sleepiness causing degree (how likely a person becomes sleepy) determined by sleepiness causing degree determiner 134 based on auxiliary information.

Specifically, corrector 131 increases or decreases the frequency of blinking of user 20 acquired by biometric information acquirer 110 based on the sleepiness causing degree determined by sleepiness causing degree determiner 134. The sleepiness causing degree is the degree indicating how likely a person becomes sleepy (the degree of how likely a person becomes sleepy).

For example, corrector 131 increases the frequency of blinking as a person is more likely to become sleepy, that is, as the sleepiness causing degree is higher. Corrector 131 decreases the frequency of blinking as a person is less likely to become sleepy, that is, as the sleepiness causing degree is lower. The rate of increase or decrease in this case is set to an appropriate value in accordance with the sleepiness causing degree and is, for example, around 0.5 to 1.5. This numerical range is merely an example, and this is not a limiting example.

Although the illustrated correction example is based on a phenomenon that the frequency of blinking increases as the sleepiness level is higher, this is not a limiting example. For example, strictly speaking, the frequency of blinking tends to decrease on the contrary when a person is very sleepy and shows a U-shaped characteristic. A correction may be made based on such a finer characteristic.

[1-2-3-2. Determiner]

Determiner 132 determines the sleepiness of a person based on biometric information corrected by corrector 131. In the present embodiment, determiner 132 determines the current sleepiness of user 20 based on corrected biometric information. Specifically, determiner 132 determines the current sleepiness level of user 20 based on the frequency of blinking of user 20.

User 20 blinks frequently to shake off his/her sleepiness, which leads to an increase in the frequency of blinking. Therefore, as illustrated in FIG. 8, determiner 132 determines the sleepiness level to be higher as the frequency of blinking is higher. On the other hand, determiner 132 determines the sleepiness level to be lower as the frequency of blinking is lower. A table or a function that defines the relationship between the sleepiness level and the frequency of blinking is stored in advance in a memory (not illustrated) or the like. Determiner 132 retrieves such a table or function from the memory and determines the sleepiness level by comparing the corrected frequency of blinking against the table or function. When there are a plurality of users 20, a table or a function that defines the relationship between the sleepiness level and the frequency of blinking may be managed for each user.

Although the frequency of blinking has been described as an example of biometric information, this is not a limiting example. For example, determiner 132 may determine the sleepiness level based on the degree of stability of the cycle of blinking. Specifically, determiner 132 may determine the sleepiness level to be lower as the cycle of blinking is more stable and determine the sleepiness level to be higher as the cycle of blinking is less stable. Furthermore, for example, determiner 132 may determine the sleepiness level based on the time it takes for user 20 to blink once. Specifically, determiner 132 may determine the sleepiness level to be lower as the time it takes for a single blink is shorter (i.e., as a person blinks faster) and determine the sleepiness level to be higher as the time it takes for a single blink is longer.

Alternatively, for example, determiner 132 may determine the sleepiness level based on a change in the line of sight. Specifically, determiner 132 may determine the sleepiness level to be lower as the line of sight changes more quickly or more frequently and determine the sleepiness level to be higher as the line of sight changes more slowly or less frequently. Furthermore, for example, determiner 132 may determine the sleepiness level based on the frequency of yawning. Specifically, determiner 132 may determine the sleepiness level to be lower as the frequency of yawning is lower and determine the sleepiness level to be higher as the frequency of yawning is higher.

[1-2-3-3. Predictor]

Predictor 133 predicts the future sleepiness based on the sleepiness determined by determiner 132 and auxiliary information. In the present embodiment, predictor 133 predicts the future sleepiness based on the sleepiness determined by determiner 132 and the sleepiness causing degree determined by sleepiness causing degree determiner 134 based on auxiliary information.

Specifically, predictor 133 raises or lowers the sleepiness level determined by determiner 132 based on the sleepiness causing degree determined by sleepiness causing degree determiner 134. For example, predictor 133 raises the sleepiness level as the sleepiness causing degree is higher and lowers the sleepiness level as the sleepiness causing degree is lower. Predictor 133 determines the raised or lowered sleepiness level as the future sleepiness.

[1-2-3-4. Sleepiness Causing Degree Determiner]

Sleepiness causing degree determiner 134 determines the sleepiness causing degree of user 20 based on auxiliary information. A person is more likely to become sleepy when the sleepiness causing degree is higher, and the sleepiness level of a person is more likely to rise along with the passage of time. A person is less likely to become sleepy when the sleepiness causing degree is lower, and a rise in the sleepiness level of a person is suppressed or the sleepiness level lowers along with the passage of time.

As with the sleepiness level, the sleepiness causing degree can be expressed, for example, in five levels—from "1" to "5". Alternatively, the sleepiness causing degree can be expressed in a value that varies continuously in a range of 0 to 1.

Specifically, sleepiness causing degree determiner 134 determines the sleepiness causing degree based on the correspondence relationship illustrated in FIG. 9. FIG. 9 illustrates an example of a relationship between auxiliary information (five-sense information) and the sleepiness causing degree (how likely a person becomes sleepy).

For example, when the category of displayed material 33 belongs to a dislike category, user 20 is not interested in displayed material 33 and is more likely to become sleepy. In contrast, when the category of displayed material 33 belongs to a like category, user 20 is interested in displayed material 33 and is less likely to become sleepy. Sleepiness causing degree determiner 134 raises the sleepiness causing degree when the category of displayed material 33 belongs to a dislike category and lowers the sleepiness causing degree when the category of displayed material 33 belongs to a like category. This applies not only to displayed material 33 but also to a sound in the surroundings of user 20.

For example, when the text size of displayed material 33 is small, user 20 needs to focus on reading the text and is more likely to become tired and sleepy. This applies similarly when the amount of text is large. In contrast, when the text size of displayed material 33 is large or when the amount of text is small, user 20 is less likely to become tired and is less likely to become sleepy.

Therefore, sleepiness causing degree determiner 134 raises the sleepiness causing degree when the text size of displayed material 33 is small and lowers the sleepiness causing degree when the text size is large. Sleepiness causing degree determiner 134 raises the sleepiness causing degree when the amount of text of displayed material 33 is large and lowers the sleepiness causing degree when the amount of text is small.

For example, when the text of displayed material 33 is displayed in black and white, displayed material 33 is monotonous, and user 20 is more likely to become bored and sleepy. This applies similarly when display 30 displaying displayed material 33 provides in a black and white display. In contrast, when the text of displayed material 33 is displayed in color or when display 30 provides a color display, user 20 is less likely to become bored with displayed material 33 and is less likely to become sleepy.

Therefore, sleepiness causing degree determiner 134 raises the sleepiness causing degree when the text of displayed material 33 is displayed in black and white and lowers the sleepiness causing degree when the text is displayed in color. Sleepiness causing degree determiner 134 raises the sleepiness causing degree when display 30 displaying displayed material 33 provides a black and white display and lowers the sleepiness causing degree when display 30 provides a color display.

For example, when display 30 displaying displayed material 33 is dim, user 20 needs to focus on recognizing displayed material 33 and is more likely to become sleepy. In contrast, when display 30 is bright, user 20 is less likely to become sleepy. Therefore, sleepiness causing degree determiner 134 raises the sleepiness causing degree when display 30 displaying displayed material 33 is dim and lowers the sleepiness causing degree when display 30 is bright.

For example, when the volume of a sound collected in the surroundings of user 20 is small, user 20 is in a quiet environment and is more likely to become sleepy. In contrast, when the volume of a sound in the surroundings of user 20 is large, user 20 is in a noisy environment and is less likely to become sleepy. Therefore, sleepiness causing degree determiner 134 raises the sleepiness causing degree when the volume of a sound is small and lowers the sleepiness causing degree when the volume of a sound is large.

For example, when a sound in the surroundings of user 20 is a music and its tempo is slow, the sound induces a relaxation effect in user 20, and user 20 is more likely to become sleepy. In contrast, when the tempo of a music is fast, the music causes user 20 to become excited, and user 20 is less likely to become sleepy. Therefore, sleepiness causing degree determiner 134 raises the sleepiness causing degree when a music is a slow-tempo music and lowers the sleepiness causing degree when a music is an up-tempo music.

For example, when a sound in the surroundings of user 20 is a conversation and a speaker in that conversation is a person with whom user 20 does not get along, user 20 does not become interested in the conversation and is more likely to become sleepy. In contrast, when a speaker in a conversation is a person whom user 20 likes, user 20 listens to the conversation with great interest and is less likely to become sleepy. Therefore, sleepiness causing degree determiner 134 raises the sleepiness causing degree when a speaker in a conversation is a person with whom user 20 does not get along and lowers the sleepiness causing degree when a speaker in a conversation is a person whom user 20 likes.

For example, when a conversation is monotonous, the user is more likely to become sleepy. In contrast, when a conversation is lively, the user is less likely to become sleepy. Therefore, sleepiness causing degree determiner 134 raises the sleepiness causing degree when a conversation is monotonous and lowers the sleepiness causing degree when a conversation is lively.

For example, when an odor in the surroundings of user 20 is an odor that has a relaxation effect, the odor provides a relaxation effect to user 20, and user 20 is more likely to become sleepy. In contrast, when an odor in the surroundings is an irritant odor, the odor induces wakefulness in user 20, and user 20 is less likely to become sleepy. Therefore, sleepiness causing degree determiner 134 raises the sleepiness causing degree when an odor has a relaxation effect and lowers the sleepiness causing degree when an odor is an irritant odor.

For example, when the amount of a meal of user 20 is large, user 20 feels full and is more likely to become sleepy. In contrast, when the amount of a meal is small, user 20 feels hungry and is less likely to become sleepy. Therefore, sleepiness causing degree determiner 134 raises the sleepiness causing degree when the amount of a meal is large and lowers the sleepiness causing degree when the amount of a meal is small.

For example, when user 20 has eaten or is eating something sweet, the blood sugar level of user 20 rises, and user 20 is more likely to become sleepy. This applies not only to something sweet to eat but also to a carbohydrate or the like. Therefore, sleepiness causing degree determiner 134 raises the sleepiness causing degree when user 20 has eaten or is eating something sweet.

For example, when user 20 has had or is having something containing caffeine, such as coffee or a tablet, user 20 is trying to shake off his/her sleepiness and is less likely to become sleepy. Therefore, sleepiness causing degree determiner 134 lowers the sleepiness causing degree when user 20 has had or is having something containing caffeine.

For example, when the frequency at which the sense of touch of user 20 is stimulated is low, user 20 is less active and is more likely to become sleepy. Alternatively, user 20 is already asleep. In contrast, when the stimulation frequency is high, user 20 is more active and is less likely to become sleepy. Therefore, sleepiness causing degree determiner 134 raises the sleepiness causing degree when the stimulation frequency is low and lowers the sleepiness causing degree when the stimulation frequency is high.

For example, when chair 13 on which user 20 is sitting is a soft chair, this chair provides a relaxation effect to user 20, and user 20 is more likely to become sleepy. In contrast, when chair 13 is a hard chair, this chair induces wakefulness in user 20, and user 20 is less likely to become sleepy. Therefore, sleepiness causing degree determiner 134 raises the sleepiness causing degree when chair 13 is soft and lowers the sleepiness causing degree when chair 13 is hard.

As described above, sleepiness causing degree determiner 134 according to the present embodiment determines the sleepiness causing degree (how likely a person becomes sleepy) in accordance with five-sense information on a stimulus for the five senses of user 20. The example illustrated in FIG. 9 illustrates an example with the five-sense information, but this is not a limiting example.

[1-3. Operation]

Figure 11:
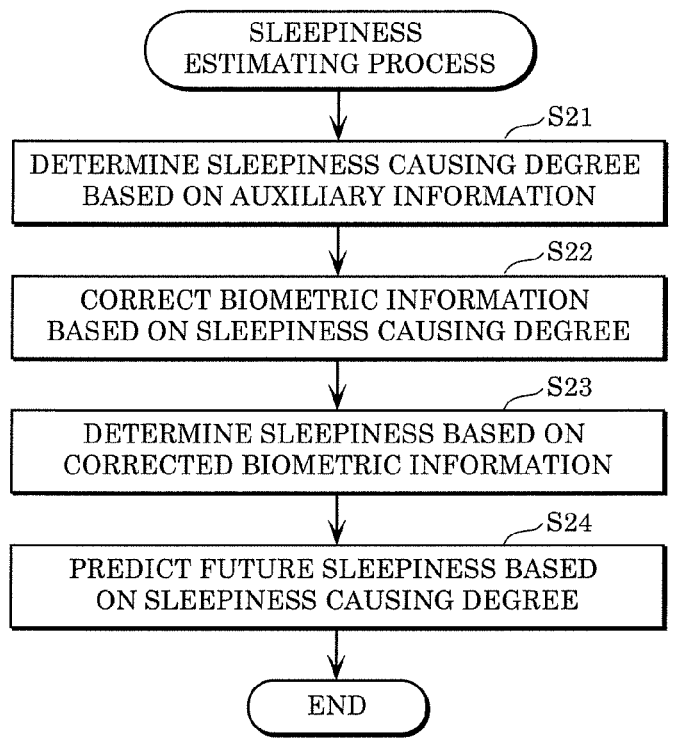
FIG. 11 is a flowchart illustrating a process of estimating the sleepiness according to Embodiment 1.

Now, with reference to FIGS. 10 and 11, an operation of sleepiness estimating device 100 according to the present embodiment will be described. FIG. 10 is a flowchart illustrating an operation of sleepiness estimating device 100 according to the present embodiment. FIG. 11 is a flowchart illustrating a process of estimating the sleepiness according to the present embodiment.

As illustrated in FIG. 10, first, sleepiness estimating device 100 acquires biometric information and auxiliary information (S10). Specifically, biometric information acquirer 110 acquires biometric information, and auxiliary information acquirer 120 acquires auxiliary information.

For example, camera 40 captures an image of the face of user 20 to generate a moving image, and biometric information acquirer 110 subjects the moving image to image processing to detect blinking. Biometric information acquirer 110 acquires, as biometric information, the number of times user 20 blinks in a predetermined period (i.e., the frequency of blinking).

In addition, for example, camera 50 captures an image of displayed material 33 to generate a moving image, and auxiliary information acquirer 120 subjects the moving image to image processing to acquire the content of displayed material 33. At this point, auxiliary information acquirer 120 may acquire the text size, the amount of text, and so on of displayed material 33.

Auxiliary information to be acquired may be only a single piece of information, or a plurality of pieces of auxiliary information may be acquired. For example, auxiliary information acquirer 120 may acquire only visual information or may acquire visual information and auditory information.

Biometric information and auxiliary information are acquired repeatedly and periodically. The time interval at which each piece of information is acquired repeatedly is, for example, one minute to several minutes or may be several seconds to several tens of seconds. As the time interval for repetition is shorter, the accuracy in estimating the sleepiness can be increased.

Next, sleepiness estimator 130 estimates the sleepiness of user 20 based on the biometric information and the auxiliary information (S20). Details of the process of estimating the sleepiness will be described below with reference to FIG. 11.

As illustrated in FIG. 11, in the process of estimating the sleepiness, first, sleepiness causing degree determiner 134 determines the sleepiness causing degree (how likely a person becomes sleepy) based on the auxiliary information (S21). Specifically, sleepiness causing degree determiner 134 determines the sleepiness causing degree based on the correspondence relationship between the auxiliary information and the sleepiness causing degree illustrated in FIG. 9. For example, when the category of displayed material 33 at which user 20 is looking belongs to a dislike category, sleepiness causing degree determiner 134 determines the sleepiness causing degree to have a high value.

Next, corrector 131 corrects the biometric information based on the sleepiness causing degree (S22). Specifically, corrector 131 increases the frequency of blinking acquired as the biometric information by biometric information acquirer 110 when the sleepiness causing degree is high and decreases the frequency of blinking when the sleepiness causing degree is low. The changed frequency of blinking serves as corrected biometric information.

Next, determiner 132 determines the current sleepiness based on the corrected biometric information (S23). Specifically, determiner 132 determines, as the current sleepiness, the sleepiness level corresponding to the frequency of blinking changed by corrector 131, based on the correspondence relationship between the frequency of blinking and the sleepiness level illustrated in FIG. 8.

Next, predictor 133 predicts the future sleepiness based on the current sleepiness and the sleepiness causing degree (S24). Specifically, predictor 133 changes the sleepiness level determined by determiner 132 in accordance with the sleepiness causing degree determined by sleepiness causing degree determiner 134. For example, predictor 133 raises the sleepiness level when the sleepiness causing degree is high and lowers the sleepiness level when the sleepiness causing degree is low. The changed sleepiness level serves as the future sleepiness.

As described above, sleepiness estimating device 100 according to the present embodiment can estimate the current sleepiness and the future sleepiness with high accuracy by using not only biometric information but also auxiliary information.

[1-4. Variations]

Now, variations of sleepiness estimating device 100 according to the present embodiment will be described. The variations illustrated below differ from the present embodiment in the configuration of sleepiness estimator 130. The following description centers on the differences from the present embodiment, and the descriptions of shared features will be omitted or simplified.

[1-4-1. Variation 1]

Figure 12:
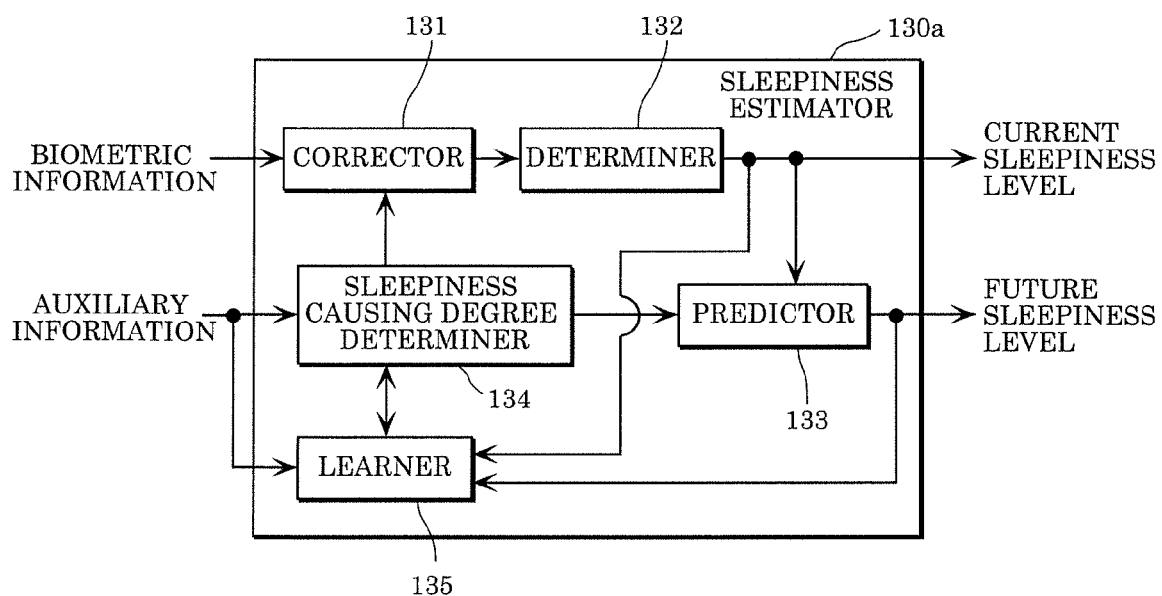
FIG. 12 is a block diagram illustrating a functional configuration of a sleepiness estimator of a sleepiness estimating device according to Variation 1 of Embodiment 1.

First, Variation 1 will be described with reference to FIG. 12. FIG. 12 is a block diagram illustrating a functional configuration of sleepiness estimator 130a of a sleepiness estimating device according to the present variation. The sleepiness estimating device according to the present variation includes sleepiness estimator 130a illustrated in FIG. 12, in place of sleepiness estimator 130 illustrated in FIGS. 2 and 4.

Figure 4:
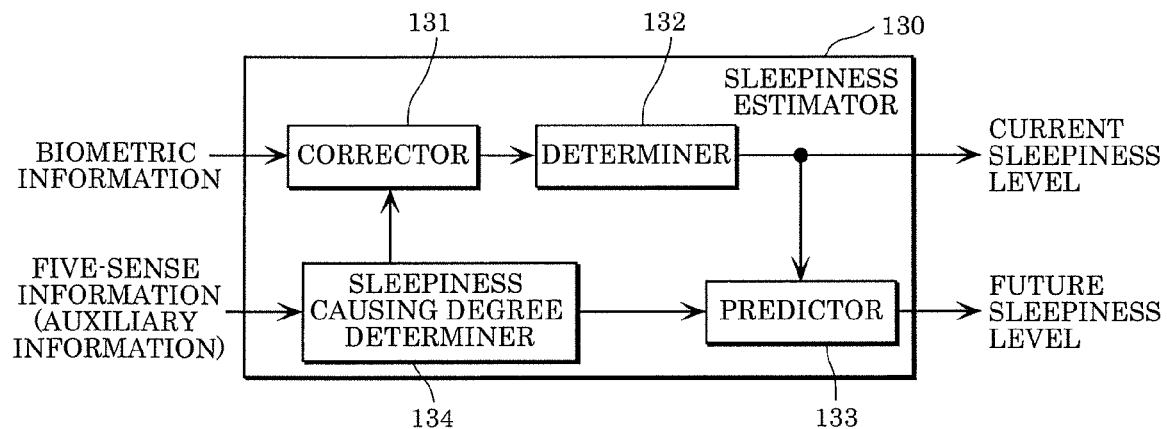
FIG. 4 is a block diagram illustrating a functional configuration of a sleepiness estimator of the sleepiness estimating device according to Embodiment 1.

As illustrated in FIG. 12, as compared with sleepiness estimator 130 illustrated in FIG. 4, sleepiness estimator 130a further includes learner 135. Learner 135 learns the preference of a person regarding displayed material 33. For example, learner 135 performs machine learning based on the categories (auxiliary information) of displayed material 33 and the estimated sleepiness of user 20 to categorize each category of displayed material 33 into a like category or a dislike category.

For example, learner 135 categorizes a category that has been determined to be associated with a high sleepiness level a large number of times into a dislike category. Furthermore, learner 135 categorizes a category that has been determined to be associated with a low sleepiness level a large number of times into a like category. There is no particular limitation on the method of learning by learner 135.

In the present variation, what learner 135 learns is not limited to the preference of a person regarding displayed material 33. For example, learner 135 may learn the preference of a person regarding music. Furthermore, learner 135 may learn the relationship between auxiliary information and the sleepiness causing degree.

[1-4-2. Variation 2]

Figure 13:
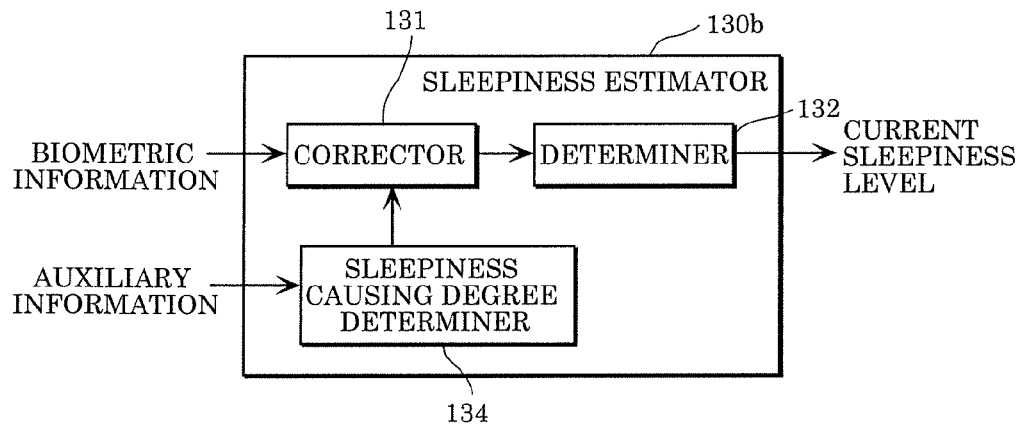
FIG. 13 is a block diagram illustrating a functional configuration of a sleepiness estimator of a sleepiness estimating device according to Variation 2 of Embodiment 1.

Next, Variation 2 will be described with reference to FIG. 13. FIG. 13 is a block diagram illustrating a functional configuration of sleepiness estimator 130b of a sleepiness estimating device according to the present variation. The sleepiness estimating device according to the present variation includes sleepiness estimator 130b illustrated in FIG. 13, in place of sleepiness estimator 130 illustrated in FIGS. 2 and 4.

As illustrated in FIG. 13, sleepiness estimator 130b differs from sleepiness estimator 130 illustrated in FIG. 4 in that sleepiness estimator 130b does not include predictor 133. In other words, sleepiness estimator 130b according to the present variation estimates only the current sleepiness of user 20.

[1-4-3. Variation 3]

Figure 14:
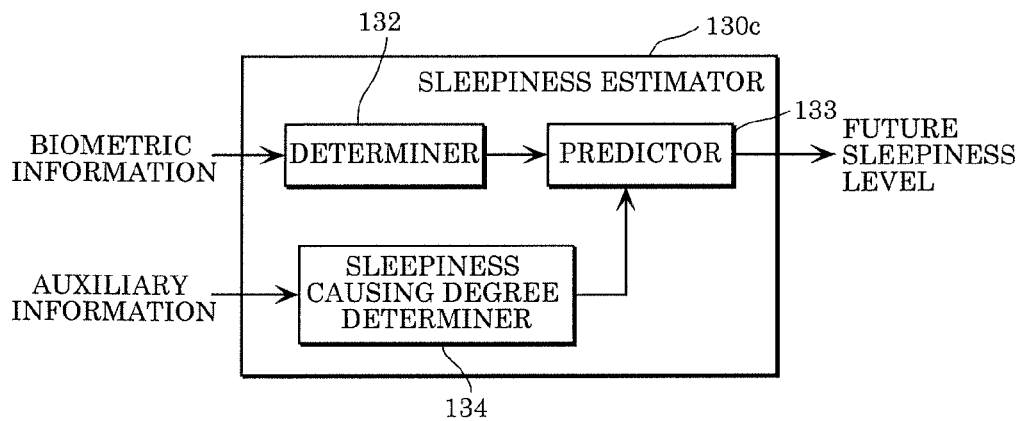
FIG. 14 is a block diagram illustrating a functional configuration of a sleepiness estimator of a sleepiness estimating device according to Variation 3 of Embodiment 1.

Next, Variation 3 will be described with reference to FIG. 14. FIG. 14 is a block diagram illustrating a functional configuration of sleepiness estimator 130c of a sleepiness estimating device according to the present variation. The sleepiness estimating device according to the present variation includes sleepiness estimator 130c illustrated in FIG. 14, in place of sleepiness estimator 130 illustrated in FIGS. 2 and 4.

As illustrated in FIG. 14, sleepiness estimator 130c differs from sleepiness estimator 130 illustrated in FIG. 4 in that sleepiness estimator 130c does not include corrector 131. Sleepiness estimator 130c according to the present variation estimates only the future sleepiness of user 20.

Specifically, in sleepiness estimator 130c according to the present variation, determiner 132 determines the current sleepiness of user 20 based not on corrected biometric information but on biometric information acquired by biometric information acquirer 110. Predictor 133 determines the future sleepiness based on the current sleepiness determined by determiner 132 and the sleepiness causing degree determined by sleepiness causing degree determiner 134.

Embodiment 2

Now, Embodiment 2 will be described.

Sleepiness estimating device according to Embodiment 1 uses five-sense information of a person as auxiliary information. Meanwhile, a sleepiness estimating device according to the present embodiment uses emotion information of a person as auxiliary information. The following description centers on the differences from Embodiment 1, and the descriptions of shared features will be omitted or simplified.

[2-1. Configuration]

First, with reference to FIGS. 15 to 17, a configuration of sleepiness estimating device 200 according to the present embodiment will be described.

Figure 15:
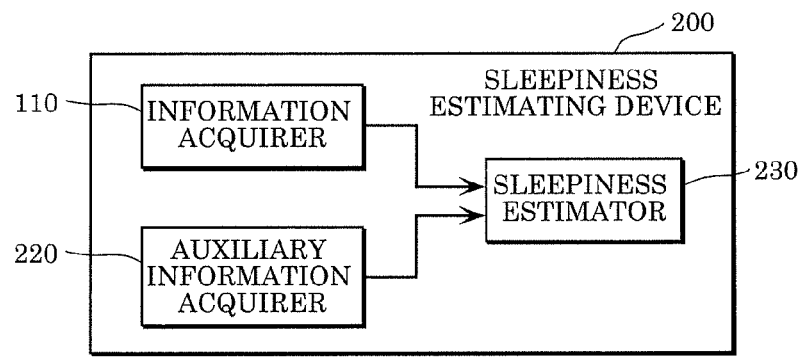
FIG. 15 is a block diagram illustrating a functional configuration of a sleepiness estimating device according to Embodiment 2.

FIG. 15 is a block diagram illustrating a functional configuration of sleepiness estimating device 200 according to the present embodiment. FIG. 16 is a block diagram illustrating a functional configuration of auxiliary information acquirer 220 of sleepiness estimating device 200 according to the present embodiment. FIG. 17 is a block diagram illustrating a functional configuration of sleepiness estimator 230 of sleepiness estimating device 200 according to the present embodiment.

As illustrated in FIG. 15, sleepiness estimating device 200 differs from sleepiness estimating device 100 illustrated in FIG. 2 in that sleepiness estimating device 200 includes auxiliary information acquirer 220 and sleepiness estimator 230, in place of auxiliary information acquirer 120 and sleepiness estimator 130.

[2-1-1. Auxiliary Information Acquirer]

Auxiliary information acquirer 220 acquires emotion information of a person as auxiliary information. Emotion information is information that indicates an emotion of a person. An Emotion of a person is categorized into one of so-called seven emotions consisting of "sad", "happy", "angry", "contempt", "disgusted", "fear", and "astonished". Emotions are not limited to the seven emotions, and an emotion may be categorized into one of 16 emotions expressed by the Russell's circumplex model of emotion. The 16 emotions include "afraid", "angry", "upset", "unpleasant", "excited", "depressed", "tired", "droopy", "bored", "relaxed", "at ease", "content", "delighted", "happy", "aroused", and "astonished".

As illustrated in FIG. 16, auxiliary information acquirer 220 includes five-sense information acquirer 221 and emotion estimator 222.

[2-1-1-1. Five-Sense information Acquirer]

Five-sense information acquirer 221 acquires five-sense information. Specifically, five-sense information acquirer 221 has a functional configuration identical to that of auxiliary information acquirer 120 illustrated in FIG. 3. In other words, five-sense information acquirer 221 includes visual information acquirer 121, auditory information acquirer 122, olfactory information acquirer 123, taste information acquirer 124, and touch information acquirer 125. It suffices that five-sense information acquirer 221 include at least one of visual information acquirer 121, auditory information acquirer 122, olfactory information acquirer 123, taste information acquirer 124, or touch information acquirer 125, and five-sense information acquirer 221 may lack one of more of the above. For example, five-sense information acquirer 221 may include only visual information acquirer 121.

[2-1-1-2. Emotion Estimator]

Emotion estimator 222 estimates an emotion of a person based on five-sense information and outputs the estimation result as emotion information of the person.

Emotion estimator 222 estimates an emotion based on displayed material 33 at which user 20 is looking, for example. For example, when displayed material 33 is an animal (pet), such as a cat, emotion estimator 222 estimates that the emotion of user 20 is "happy". For example, when displayed material 33 is news or the like on a gloomy incident, emotion estimator 222 estimates that the emotion of user 20 is at least one of "angry", "contempt", or "fear". The number of emotions estimated by emotion estimator 222 may be more than one.

[2-1-2. Sleepiness Estimator]

Sleepiness estimator 230 estimates the sleepiness of a person based on biometric information and auxiliary information. In the present embodiment, sleepiness estimator 230 estimates the current sleepiness and the future sleepiness of a person based on biometric information and emotion information.

As illustrated in FIG. 17, sleepiness estimator 230 differs from sleepiness estimator 130 illustrated in FIG. 4 in that sleepiness estimator 230 includes sleepiness causing degree determiner 234 in place of sleepiness causing degree determiner 134. As illustrated in Variations 2 and 3 of Embodiment 1, sleepiness estimator 230 may estimate only the current sleepiness of a person or estimate only the future sleepiness of a person.

Sleepiness causing degree determiner 234 determines the sleepiness causing degree of user 20 based on emotion information. Specifically, sleepiness causing degree determiner 234 determines the sleepiness causing degree based on the correspondence relationship illustrated in FIG. 18. FIG. 18 illustrates an example of a relationship between auxiliary information (emotion information) and the sleepiness causing degree (how likely a person becomes sleepy).

For example, when an emotion indicated by emotion information is a mild emotion, wakefulness is less likely to be induced in user 20, and user 20 is more likely to become sleepy. In contrast, when an emotion indicated by emotion information is an intense emotion, wakefulness is induced in user 20, and user 20 is less likely to become sleepy. Therefore, sleepiness causing degree determiner 234 raises the sleepiness causing degree when an emotion indicated by emotion information is a mild emotion and lowers the sleepiness causing degree when an indicated emotion is an intense emotion.

The intensity of each emotion is defined in advance for each type of emotion and stored in a memory or the like. Alternatively, the intensity of each emotion may be defined based on the Russell's circumplex model of emotion. For example, an emotion such as "astonished" or "angry" is categorized into an intense emotion, and an emotion such as "droopy" or "bored" is categorized into a mild emotion.

For example, when an emotion indicated by emotion information is a pleasant emotion, this has a relaxation effect on user 20, and user 20 is more likely to become sleepy. In contrast, when an emotion indicated by emotion information is an unpleasant emotion, user 20 is less likely to become sleepy. Therefore, sleepiness causing degree determiner 234 raises the sleepiness causing degree when an emotion indicated by emotion information is a pleasant emotion and lowers the sleepiness causing degree when an indicated emotion is an unpleasant emotion.

Whether a given emotion is a pleasant or unpleasant emotion is defined in advance for each type of emotion and stored in a memory or the like. Alternatively, whether a given emotion is a pleasant or unpleasant emotion may be defined based on the Russell's circumplex model of emotion. For example, an emotion such as "happy" or "content" is categorized into a pleasant emotion, and an emotion such as "sad" or "depressed" is categorized into an unpleasant emotion.

As described above, sleepiness causing degree determiner 234 according to the present embodiment determines the sleepiness causing degree (how likely a person becomes sleepy) in accordance with emotion information of user 20. The example described above illustrates an example with emotion information, but this is not a limiting example.

[2-2. Operation]

Figure 19:
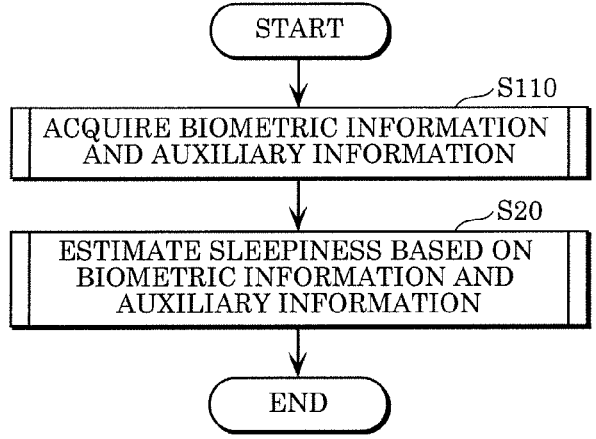
FIG. 19 is a flowchart illustrating an operation of the sleepiness estimating device according to Embodiment 2.
Figure 20:
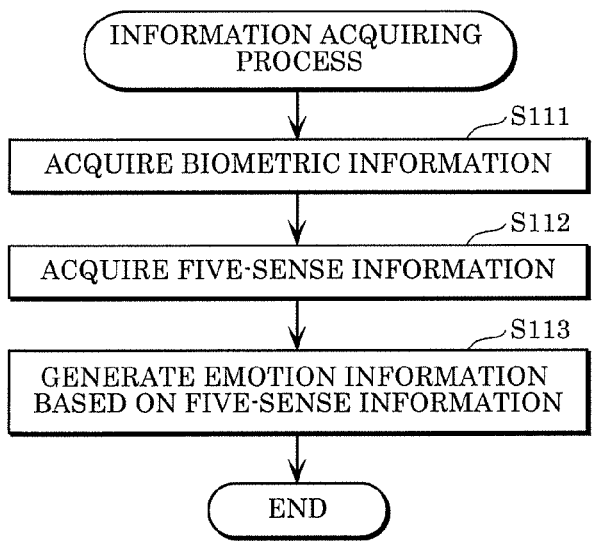
FIG. 20 is a flowchart illustrating a process of acquiring information according to Embodiment 2.

Now, with reference to FIGS. 19 and 20, an operation of sleepiness estimating device 200 according to the present embodiment will be described. FIG. 19 is a flowchart illustrating an operation of sleepiness estimating device 200 according to the present embodiment. FIG. 20 is a flowchart illustrating a process of acquiring information according to the present embodiment.

As illustrated in FIG. 19, first, sleepiness estimating device 200 acquires biometric information and auxiliary information (S110). Details of the process of acquiring these pieces of information will be described below with reference to FIG. 20.

As illustrated in FIG. 20, first, biometric information acquirer 110 acquires biometric information (S111). For example, camera 40 captures an image of the face of user 20 to generate a moving image, and biometric information acquirer 110 subjects the moving image to image processing to detect blinking. Biometric information acquirer 110 acquires, as the biometric information, the number of times user 20 blinks in a predetermined period (i.e., the frequency of blinking).

Next, five-sense information acquirer 221 acquires five-sense information (S112). For example, camera 50 captures an image of displayed material 33 to generate a moving image, and five-sense information acquirer 221 subjects the moving image to image processing to acquire the content of displayed material 33. The five-sense information may be acquired before the biometric information is acquired or simultaneously when the biometric information is acquired.

Next, emotion estimator 222 generates emotion information based on the five-sense information (S113). For example, emotion estimator 222 estimates an emotion based on displayed material 33 at which user 20 is looking. For example, when displayed material 33 is an animal (pet), such as a cat, emotion estimator 222 estimates that the emotion of user 20 is "happy".

Referring back to FIG. 19, next, sleepiness estimator 230 estimates the sleepiness of user 20 with use of the biometric information and the auxiliary information (specifically, the emotion information) (S20). Details of the process of estimating the sleepiness is the same as those described with reference to FIG. 11. In the present embodiment, sleepiness estimator 230 estimates the current sleepiness and the future sleepiness with use of the emotion information as the auxiliary information.

As described above, sleepiness estimating device 200 according to the present embodiment can estimate the current sleepiness and the future sleepiness with high accuracy by using not only biometric information but also emotion information.

An emotion of a person greatly affects his/her sleepiness. For example, a person is less likely to become sleepy when he/she is in an aroused state and is more likely to become sleepy when he/she is in a relaxed state. Therefore, the use of not only biometric information but also emotion information makes it possible to increase the accuracy in estimating the sleepiness.

[2-3. Variations]

Now, variations of sleepiness estimating device 200 according to the present embodiment will be described. The variations illustrated below differ from the present embodiment in the configuration of auxiliary information acquirer 220. The following description centers on the differences from the present embodiment, and the descriptions of shared features will be omitted or simplified.

[2-3-1. Variation 1]

Figure 21:
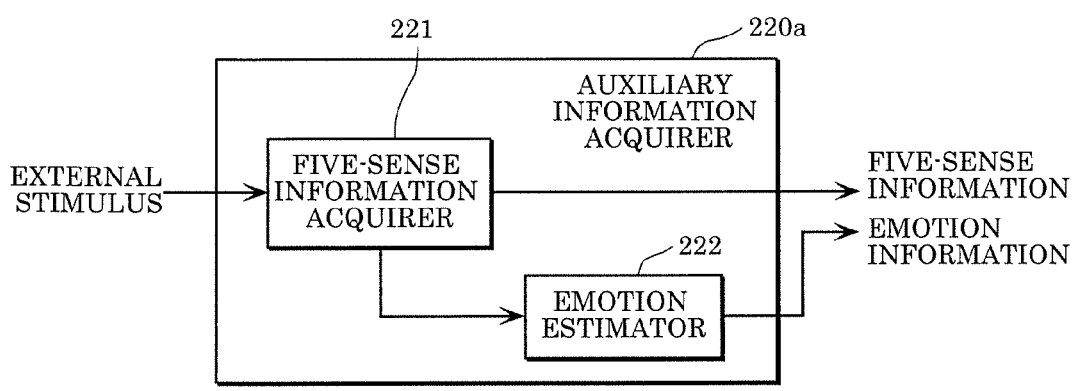
FIG. 21 is a block diagram illustrating a functional configuration of an auxiliary information acquirer of a sleepiness estimating device according to Variation 1 of Embodiment 2.

First, Variation 1 will be described with reference to FIG. 21. FIG. 21 is a block diagram illustrating a functional configuration of auxiliary information acquirer 220a of a sleepiness estimating device according to the present variation. The sleepiness estimating device according to the present variation includes auxiliary information acquirer 220a illustrated in FIG. 21, in place of auxiliary information acquirer 220 illustrated in FIGS. 15 and 16.

As illustrated in FIG. 21, auxiliary information acquirer 220a outputs not only emotion information but also five-sense information. In other words, auxiliary information acquirer 220a outputs both five-sense information and emotion information to sleepiness estimator 230.

With this configuration, the sleepiness estimating device according to the present variation estimates the sleepiness with use of both five-sense information and emotion information, and thus the accuracy in estimating the sleepiness can be further increased.

[2-3-2. Variation 2]

Figure 22:
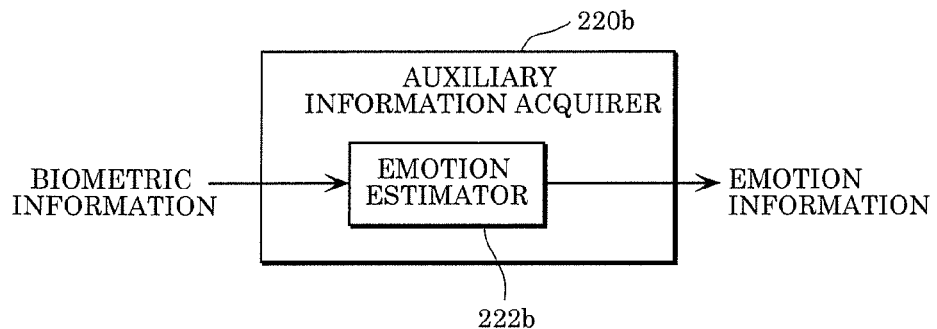
FIG. 22 is a block diagram illustrating a functional configuration of an auxiliary information acquirer of a sleepiness estimating device according to Variation 2 of Embodiment 2.

Next, Variation 2 will be described with reference to FIG. 22. FIG. 22 is a block diagram illustrating a functional configuration of auxiliary information acquirer 220b of a sleepiness estimating device according to the present variation. The sleepiness estimating device according to the present variation includes auxiliary information acquirer 220b illustrated in FIG. 22, in place of auxiliary information acquirer 220 illustrated in FIGS. 15 and 16.

As illustrated in FIG. 22, auxiliary information acquirer 220b includes only emotion estimator 222b. Emotion estimator 222b estimates an emotion of a person based on biometric information and outputs the estimation result as emotion information.

For example, based on a captured image obtained as camera 40 captures an image of the face of user 20, biometric information acquirer 110 acquires the facial expression of user 20 as biometric information. Alternatively, based on audio information obtained as a microphone collects a sound in the surroundings of user 20, biometric information acquirer 110 may acquire the voice of user 20 as biometric information.

Emotion estimator 222b estimates an emotion based on the facial expression, the voice quality, or the like of user 20. Specifically, emotion estimator 222b analyzes the facial expression based on the state of facial parts, such as the eyes and the mouth, of user 20 and estimates an emotion. For example, when user 20 has a facial expression where the corners of the eyes point downward and the corners of the mouth are firmly pulled downward, emotion estimator 222b estimates that the emotion of user 20 is "sad". Alternatively, when a sound of laughter of user 20 is collected, emotion estimator 222b may estimate that the emotion of user 20 is "delighted".

Now, an operation of the sleepiness estimating device according to the present variation will be described. The operation of the sleepiness estimating device according to the present variation differs from that of Embodiment 2 only in the process of acquiring information.

Figure 23:
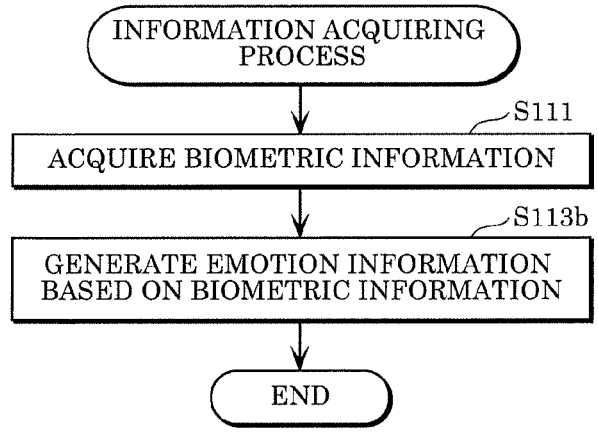
FIG. 23 is a flowchart illustrating a process of acquiring information according to Variation 2 of Embodiment 2.

FIG. 23 is a flowchart illustrating a process of acquiring information according to the present variation.

As illustrated in FIG. 23, first, biometric information acquirer 110 acquires biometric information (S111). Next, emotion estimator 222b generates emotion information based on the biometric information (S113b)

In this manner, the sleepiness estimating device according to the present variation does not need to acquire five-sense information, and the sleepiness estimating device acquires biometric information and generates emotion information based on the acquired biometric information. This renders a component, such as camera 50, for acquiring five-sense information unnecessary, and thus the configuration of the sleepiness estimating device can be simplified.

Although an example in which an emotion of a person is estimated based on biometric information or five-sense information has been described in the present embodiment and the variations thereof, this is not a limiting example. The emotion estimator may estimate an emotion of user 20 based on information input by user 20 or a manager.

For example, the emotion estimator acquires schedule information of user 20. Schedule information is information that indicates an activity plan of user 20, and the time and an activity (action) plan are associated with each other in schedule information. Specifically, when the emotion estimator is to estimate an emotion of user 20 held at a predetermined time, the emotion estimator uses an activity of user 20 planned at the predetermined time or an activity of user 20 planned immediately before or immediately after the predetermined time.

For example, when user 20 is going to be in a meeting or is in a meeting with a company executive, the emotion estimator may estimate that the emotion of user 20 is "stressed". When the meeting is over, the emotion estimator may estimate that the emotion of user 20 is "relaxed". Alternatively, when user 20 is having lunch with a coworker, the emotion estimator may estimate that the emotion of user 20 is "delighted".

In this manner, there is no particular limitation on the method of estimating an emotion of a person in the sleepiness estimating device.

Embodiment 3

Now, Embodiment 3 will be described. Described in Embodiment 3 is a wakefulness inducing device that induces wakefulness in a person based on the sleepiness estimated in Embodiment 1 or 2 or the variations thereof described above.

[3-1. Configuration]

First, with reference to FIGS. 24 and 25, a configuration of wakefulness inducing device 300 according to the present embodiment will be described.

Figure 24:
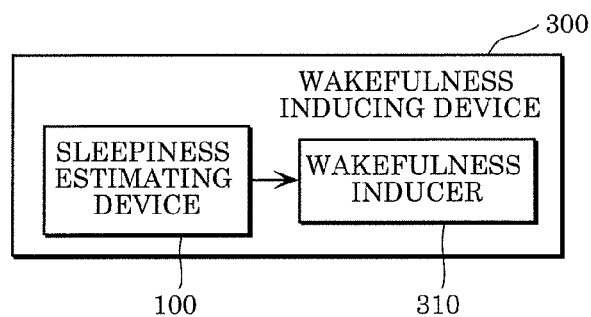
FIG. 24 is a block diagram illustrating a functional configuration of a wakefulness inducing device according to Embodiment 3.
Figure 25:
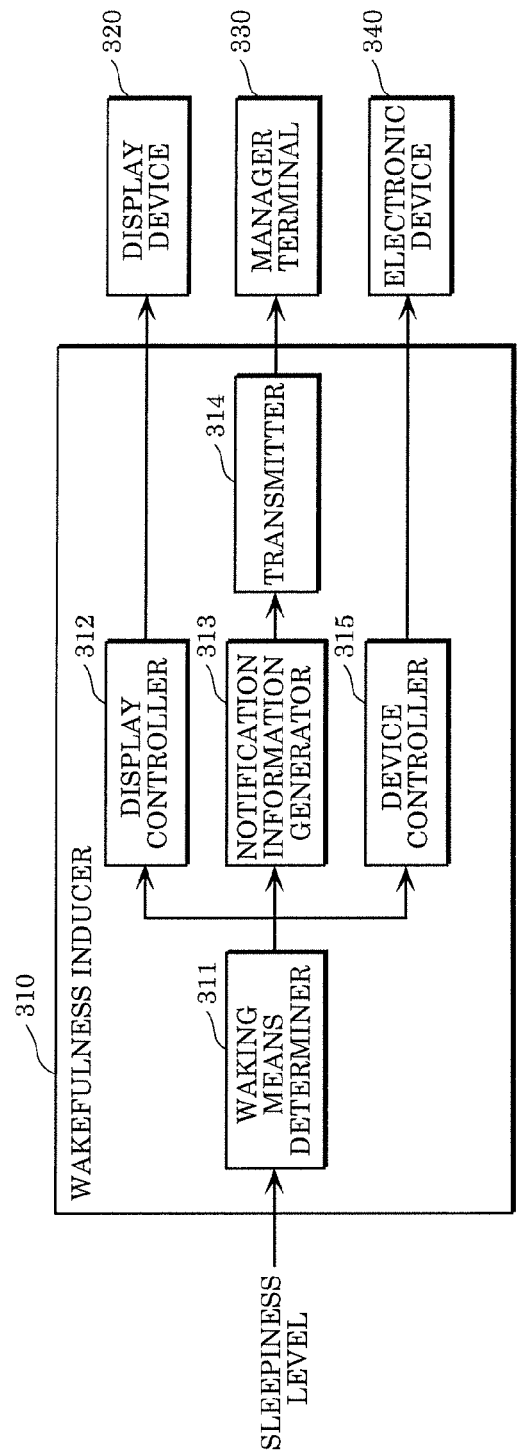
FIG. 25 is a block diagram illustrating a functional configuration of a wakefulness inducer of the wakefulness inducing device according to Embodiment 3.

FIG. 24 is a block diagram illustrating a functional configuration of wakefulness inducing device 300 according to the present embodiment. FIG. 25 is a block diagram illustrating a functional configuration of wakefulness inducer 310 of wakefulness inducing device 300 according to the present embodiment.

As illustrated in FIG. 24, wakefulness inducing device 300 includes sleepiness estimating device 100 and wakefulness inducer 310. Sleepiness estimating device 100 is the same as sleepiness estimating device 100 described in Embodiment 1, and thus descriptions thereof will be omitted below.

Wakefulness inducing device 300 may include sleepiness estimating device 100 according to the variations of Embodiment 1 or sleepiness estimating device 200 according to Embodiment 2 or the variations thereof, in place of sleepiness estimating device 100.

[3-2. Wakefulness Inducer]

Wakefulness inducer 310 induces wakefulness in a person based on the sleepiness estimated by sleepiness estimator 130 of sleepiness estimating device 100. Specifically, as illustrated in FIG. 25, wakefulness inducer 310 includes waking means determiner 311, display controller 312, notification information generator 313, transmitter 314, and device controller 315.

Wakefulness inducer 310 is implemented by a non-volatile memory storing a program, a volatile memory serving as a temporary storage area for executing a program, an input/output port, a processor that executes a program, and so on, for example.

Although display device 320, manager terminal 330, and electronic device 340 are illustrated as examples of a device for inducing wakefulness in user 20 in the present embodiment, these are merely examples. A device for inducing wakefulness may be only one of display device 320, manager terminal 330, and electronic device 340. Wakefulness inducer 310 may include only one of display controller 312, a set of notification information generator 313 and transmitter 314, and device controller 315.

[3-2-1. Waking Means Determiner]

Waking means determiner 311 determines a means (waking means) for inducing wakefulness in user 20. Specifically, waking means determiner 311 determines a device for inducing wakefulness in user 20.

In the present embodiment, waking means determiner 311 determines whether to induce wakefulness in user 20 based on the sleepiness level estimated by sleepiness estimating device 100. Specifically, when the sleepiness level is higher than a predetermined threshold, waking means determiner 311 determines to induce wakefulness in user 20 and determines a waking means.

At this point, waking means determiner 311 determines a waking means based on the current sleepiness of user 20. For example, waking means determiner 311 determines a waking means with a higher waking degree as the sleepiness level is higher. Meanwhile, waking means determiner 311 determines a waking means with a lower waking degree as the sleepiness level is lower. Waking means determiner 311 may determine a waking means determined in advance by user 20 or a manager.

[3-2-2. Display Controller]

Display controller 312 controls the display on display device 320. Specifically, display controller 312 changes an image displayed on display device 320. For example, display device 320 is a display of an electronic device operated by user 20. Display device 320 may be display 30 illustrated in FIG. 1.

An image to be changed to is selected in accordance with an environment surrounding user 20, for example. For example, when user 20 belongs to office environment 10 illustrated in FIG. 1, display controller 312 displays, on display device 320, an image prompting user 20 to perform a predetermined operation.

Figure 26:
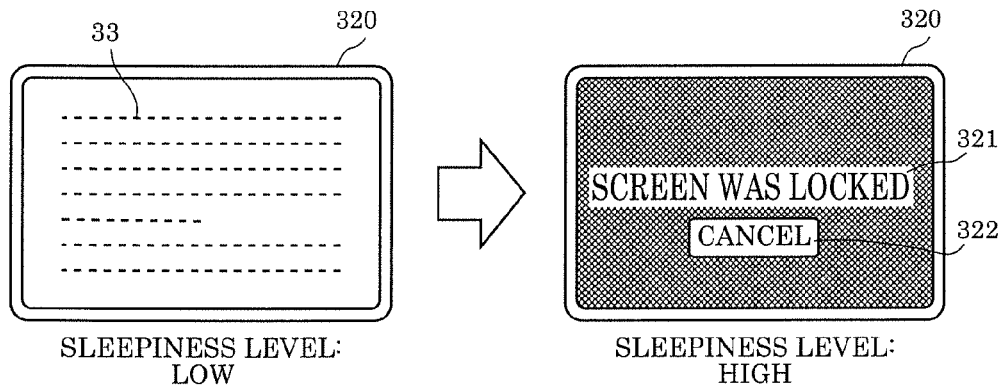
FIG. 26 illustrates an example of a change in a display screen caused by the wakefulness inducer according to Embodiment 3.

FIG. 26 illustrates an example of a change in a display screen caused by wakefulness inducer 310 according to the present embodiment. As illustrated in FIG. 26, when the sleepiness level is low, displayed material 33 such as a text is displayed on display device 320.

When the sleepiness level has risen, display controller 312 displays lock image 321 instead of displayed material 33 on display device 320. Lock image 321 displays cancel button 322. When user 20 clicks (presses) cancel button 322 with use of keyboard 31 or mouse 32, display controller 312 restores the display to the state held before lock image 321 was displayed. In other words, display device 320 displays displayed material 33.

As user 20 is prompted to click cancel button 322 in this manner, wakefulness can be induced in user 20. Lock image 321 may be an image that differs from displayed material 33 in at least one of the luminance or the tone. This can make user 20 realize more easily that the display screen has changed through a change in the luminance or the color.

Display controller 312 may stop the display on display device 320 instead of displaying lock image 321. Specifically, when the sleepiness level is high, a black screen is displayed on display device 320. Display controller 312 resumes the display of displayed material 33 when user 20 operates mouse 32 or the like.

Figure 27:
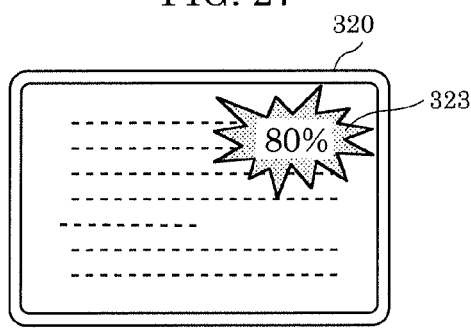
FIG. 27 illustrates a display example on a display device displayed by the wakefulness inducer according to Embodiment 3.

For example, when user 20 belongs to a learning environment, such as an after-school learning center or a school, display controller 312 may display an image that provides notification 323 to user 20 on display device 320, as illustrated in FIG. 27. FIG. 27 illustrates a display example on display device 320 displayed by wakefulness inducer 310 according to the present embodiment.

Notification 323 indicates the probability that user 20 will be picked next by a teacher to solve a problem or the like. As illustrated in FIG. 27, displaying a high probability of "80%" can make user 20 feel more tense and induce wakefulness in user 20. The teacher may also be notified of this probability. As the teacher is notified, the teacher can actually pick user 20, and this can help keep the reliability of the displayed probability high.

[3-2-3. Notification Information Generator]

Figure 28:
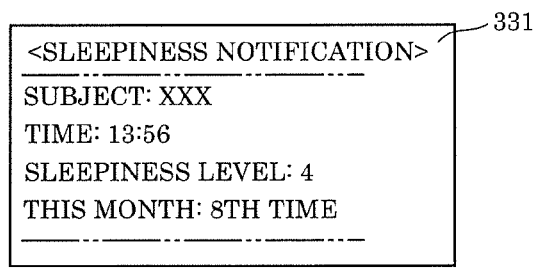
FIG. 28 illustrates an example of notification information generated by the wakefulness inducer according to Embodiment 3.

Notification information generator 313 generates notification information 331 for notifying user 20 of information regarding the sleepiness of user 20. As illustrated in FIG. 28, notification information 331 includes information on a subject (user 20), information on the time, and information on the sleepiness level, for example. FIG. 28 illustrates an example of notification information generated by wakefulness inducer 310 according to the present embodiment.

The information on the subject is information for identifying user 20, such as the name or an ID number (e.g., employee number) of user 20, for example. The information on the time indicates the time at which the sleepiness of user 20 is detected or the time at which the notification information is generated, for example. The information on the sleepiness level is information indicating the sleepiness level of user 20.

Notification information 331 may further include count information indicating the number of times the notification has been made. The count information is information indicating the number of times user 20 has been notified within a predetermined duration, such as one day, one week, or one month. For example, notification information 331 illustrated in FIG. 28 indicates that user 20 has been notified eight times this month.

[3-2-4. Transmitter]

Transmitter 314 transmits notification information 331 generated by notification information generator 313 to manager terminal 330. For example, transmitter 314 is implemented by a communication IF or the like and transmits notification information 331 to manager terminal 330 through wired communication, wireless communication, or the like.

Figure 29:
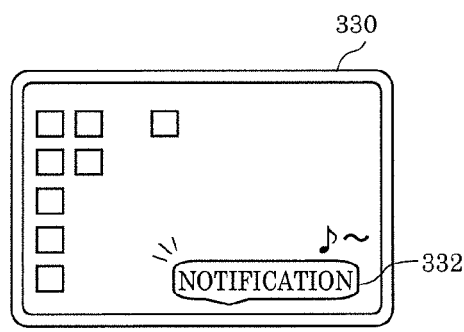
FIG. 29 illustrates an example of a screen display on a manager terminal displayed by the wakefulness inducer according to Embodiment 3.

FIG. 29 illustrates an example of a display screen on manager terminal 330 displayed by wakefulness inducer 310 according to the present embodiment. When transmitter 314 has transmitted notification information 331, notification image 332 indicating that notification information 331 has been received is displayed on a display screen of manager terminal 330. When notification image 332 is clicked, notification information 331 illustrated in FIG. 28 is displayed on the display screen of manager terminal 330.

This allows a manager to be notified that the sleepiness level of user 20 is high. The manager is a supervisor or the like of user 20, for example. Upon being notified that the sleepiness level of user 20 is high, the manager can take an action, such as inducing wakefulness in user 20. In addition, the manager can reflect the information on the evaluation of user 20 regarding his/her attitude toward work.

For example, the manager lets user 20 know in advance that the manager, such as a supervisor, will be notified when the sleepiness level of user 20 is high. This can make user 20 stay tense, and wakefulness can be induced in user 20.

Although an example in which transmitter 314 transmits notification information 331 to manager terminal 330 has been illustrated, this is not a limiting example. For example, transmitter 314 may output notification information 331 to a speaker or the like in the form of audio data. The speaker is, for example, an audio output device installed on the ceiling and outputs a sound to the surroundings of user 20.

As notification information 331 is output from the speaker or the like in the form of a sound, not only user 20 but also a person (e.g., supervisor, coworker, etc.) in the surroundings of user 20 is notified of the sleepiness level of user 20. This can act on the sense of shame of user 20 and can make user 20 stay tense, and wakefulness can be induced in user 20.

[3-2-5. Device Controller]

Device controller 315 controls electronic device 340. Specifically, device controller 315 causes electronic device 340 to perform an operation for inducing wakefulness in user 20 in accordance with a function of electronic device 340.

Figure 30:
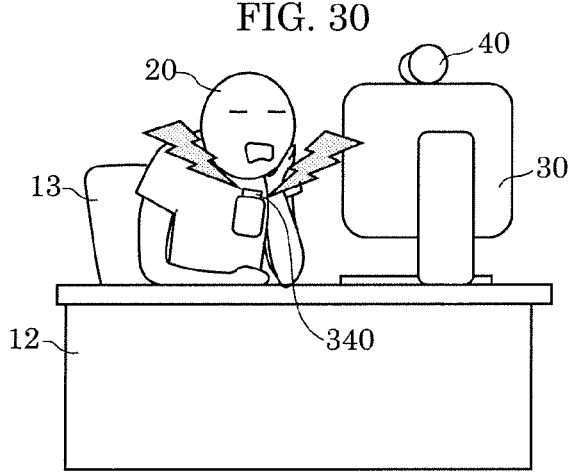
FIG. 30 illustrates an example of control of an electronic device performed by the wakefulness inducer according to Embodiment 3.

FIG. 30 illustrates an example of control of electronic device 340 performed by wakefulness inducer 310 according to the present embodiment. In the present embodiment, electronic device 340 is a mobile terminal, such as a smartphone, of user 20. As illustrated in FIG. 30, electronic device 340 is placed in a pocket of clothing of user 20, for example.

Device controller 315 calls electronic device 340, for example. Upon the call coming in to electronic device 340, electronic device 340 outputs a ring tone and/or vibrates with a vibrator. This auditory stimulus or vibration stimulates the sense of touch, and thus wakefulness can be induced in user 20. Furthermore, by answering the phone, wakefulness can be further induced in user 20.

Electronic device 340 to be controlled by device controller 315 is not limited to a smartphone. For example, device controller 315 may control a speaker (not illustrated) or display 30 present in the surroundings of user 20. Specifically, device controller 315 may output a predetermined question through the speaker in the form of a sound and make user 20 answer that question. In a similar manner, device controller 315 may display a question on display 30 in text and make user 20 answer the question. By making user 20 use his/her brain, wakefulness can be induced in user 20.

[3-3. Operation]

Figure 31:
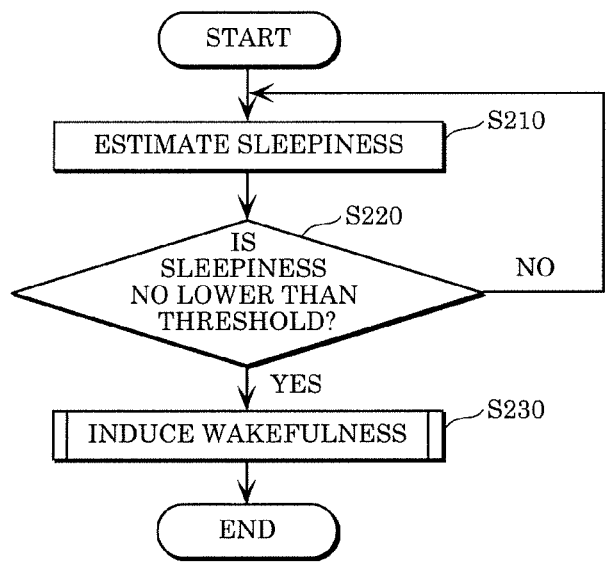
FIG. 31 is a flowchart illustrating an operation of the wakefulness inducing device according to Embodiment 3.
Figure 32:
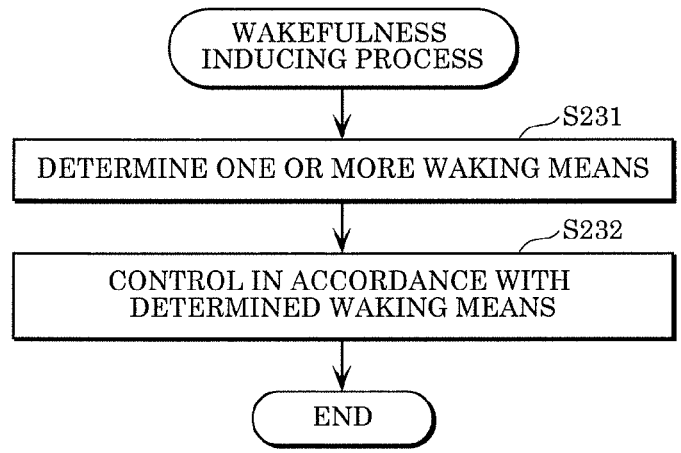
FIG. 32 is a flowchart illustrating a wakefulness inducing process according to Embodiment 3.

Now, with reference to FIGS. 31 and 32, an operation of wakefulness inducing device 300 according to the present embodiment will be described. FIG. 31 is a flowchart illustrating an operation of wakefulness inducing device 300 according to the present embodiment. FIG. 32 is a flowchart illustrating a wakefulness inducing process according to the present embodiment.

First, as illustrated in FIG. 31, wakefulness inducing device 300 estimates the sleepiness of user 20 (S210). Specifically, sleepiness estimating device 100 of wakefulness inducing device 300 estimates the sleepiness level of user 20. The specific process is the same as that described in Embodiment 1 and so on. The sleepiness level is estimated periodically, for example, every one minute or the like.

Next, waking means determiner 311 determines whether the estimated sleepiness level is no lower than a threshold (S220). For example, when the sleepiness level is expressed in five levels, as illustrated in FIG. 8, the threshold is "3". This threshold is merely an example.

When the sleepiness level is lower than the threshold (NO in S220), the process returns to step S210, and sleepiness estimating device 100 stands by until the next sleepiness level is estimated. When the sleepiness level is no lower than the threshold (YES in S220), wakefulness inducer 310 performs a process of inducing wakefulness in user 20 (S230). The specific process will be described with reference to FIG. 32.

As illustrated in FIG. 32, in the wakefulness inducing process, first, waking means determiner 311 determines one or more waking means (S231). For example, waking means determiner 311 determines a waking means corresponding to the estimated sleepiness level.

Next, wakefulness inducer 310 performs control in accordance with the determined waking means (S232). For example, when a change in the display on display device 320 is determined to be a waking means, display controller 312 displays lock image 321 on display device 320. This applies similarly when generation of notification information 331 or control of electronic device 340 is determined as a waking means.

As described above, wakefulness inducing device 300 according to the present embodiment can induce wakefulness in a person based on the sleepiness estimated with high accuracy, and this makes it possible to shake off the person's sleepiness with high efficiency. Therefore, the amount of energy consumed to induce wakefulness can be reduced, the power consumption can be reduced, and the energy can be saved, for example.

The method of inducing wakefulness described in the present embodiment is merely an example, and a different method may be used instead. For example, the wakefulness inducer may control air conditioning equipment, such as an air conditioner; an audio output device, such as an alarm; an illumination device that emits light; or the like.

An example in which the wakefulness inducer according to the present embodiment induces wakefulness based on the current sleepiness has been described. Alternatively, the wakefulness inducer may induce wakefulness based on the future sleepiness. For example, the wakefulness inducer may have a timer function (scheduling function) and induce wakefulness at a future time at which the sleepiness level will have become no lower than the threshold.

Embodiment 4

Now, Embodiment 4 will be described.

Described in Embodiment 4 is a sleepiness estimating device that estimates the sleepiness of a driver driving a moving body, such as an automobile, or of a passenger onboard a moving body and a wakefulness inducing device that induces wakefulness in the driver or the passenger. Specifically, the sleepiness estimating device according to the present embodiment acquires route information on a planned route of a moving body as auxiliary information and estimates the sleepiness of a driver or a passenger based on the acquired route information.

[4-1. Configuration]

First, with reference to FIGS. 33 to 35, a configuration of the sleepiness estimating device according to the present embodiment and a configuration of the wakefulness inducing device that includes the sleepiness estimating device will be described.

Figure 33:
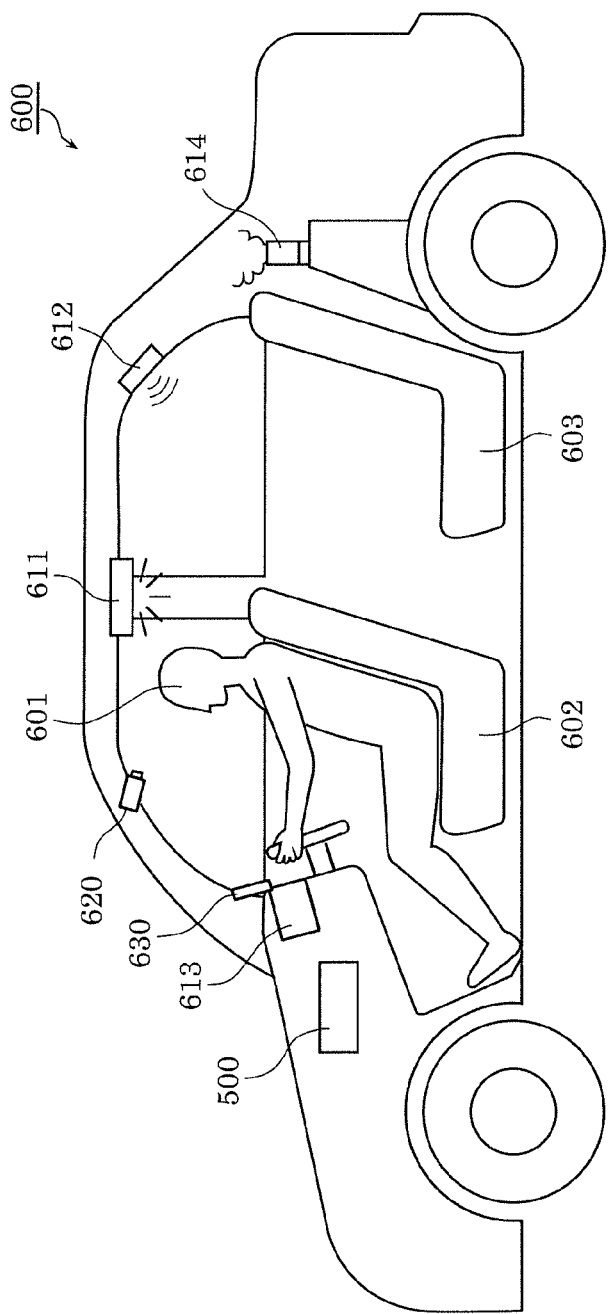
FIG. 33 is a schematic diagram illustrating a vehicle provided with a wakefulness inducing device according to Embodiment 4.

FIG. 33 is a schematic diagram illustrating vehicle 600 provided with wakefulness inducing device 500 according to the present embodiment. FIG. 34 is a block diagram illustrating a functional configuration of wakefulness inducing device 500 according to the present embodiment. FIG. 35 is a block diagram illustrating a functional configuration of sleepiness estimator 430 of sleepiness estimating device 400 according to the present embodiment.

Wakefulness inducing device 500 according to the present embodiment is provided in vehicle 600 illustrated in FIG. 33, for example. First, vehicle 600 will be described.

Vehicle 600 is an example of a moving body, such as a four-wheeled automobile. Vehicle 600 is not limited to a four-wheeled automobile and may be a train, a ship, an aircraft, or the like. As illustrated in FIG. 33, vehicle 600 is provided with driver's seat 602 on which driver 601 driving vehicle 600 is sits and backseat 603 on which a passenger (not illustrated) who is not driving sits.

Vehicle 600 is further provided with illumination device 611, speaker 612, air-conditioning device 613, and scent-emitting device 614. Illumination device 611 is an in-vehicle (interior) illumination device that illuminates the interior of vehicle 600, and illumination device 611 emits illumination light (visible light). Speaker 612 outputs a sound into vehicle 600. Air-conditioning device 613 is an air conditioner or the like that regulates the temperature (room temperature) inside vehicle 600. Air-conditioning device 613 may generate an airflow and blow the air toward driver's seat 602. Scent-emitting device 614 is an aroma diffuser or the like that emits a scent.

Vehicle 600 is further provided with camera 620 for capturing an image of driver 601. Camera 620 is a camera for acquiring biometric information of driver 601 and captures an image of the face of driver 601, for example. Camera 620 is the same as camera 40 according to Embodiment 1.

Vehicle 600 is further provided with display 630. Display 630 is, for example, a touch panel display and can receive an operation from driver 601. For example, vehicle 600 includes a car navigation system (not illustrated). Display 630 functions as an input/output device of the car navigation system.

[4-1-1. Wakefulness Inducing Device]

Wakefulness inducing device 500 induces wakefulness in driver 601. As illustrated in FIG. 33, wakefulness inducing device 500 is installed, for example, in an instrument panel of vehicle 600. Wakefulness inducing device 500 is connected to at least one of illumination device 611, speaker 612, air-conditioning device 613, or scent-emitting device 614 provided in vehicle 600. Wakefulness inducing device 500 induces wakefulness in driver 601 by controlling at least one of illumination device 611, speaker 612, air-conditioning device 613, or scent-emitting device 614. Wakefulness inducing device 500 may induce wakefulness in a passenger who is not driving vehicle 600.

As illustrated in FIG. 34, wakefulness inducing device 500 includes sleepiness estimating device 400, wakefulness inducer 310, and receiver 520. Sleepiness estimating device 400 includes biometric information acquirer 110 and auxiliary information acquirer 420. Auxiliary information acquirer 420 includes five-sense information acquirer 221 and route information acquirer 422. Wakefulness inducer 310, biometric information acquirer 110, and five-sense information acquirer 221 are the same as those illustrated in Embodiments 1 to 3, and thus descriptions thereof will be omitted or simplified below.

[4-1-2. Route Information Acquirer]

Route information acquirer 422 acquires route information, which is an example of auxiliary information. Route information is information on a planned route of vehicle 600. Specifically, route information includes information indicating a route from a current location to a destination and the condition of the route.

FIG. 36 illustrates route information to be acquired by sleepiness estimating device 400 according to the present embodiment. FIG. 37 illustrates map 700 including the route information illustrated in FIG. 36.

Map 700 shows current location 710, destination 720, route 730 from current location 710 to destination 720, and detailed information 740 on route 730. Map 700 may be displayed on display 630 included in vehicle 600, for example.

Current location 710 is a current location of vehicle 600 and is acquired by a location-finding system, such as the Global Positioning System (GPS). Destination 720 is acquired as driver 601 sets destination 720 in the car navigation system, for example.

Route 730 is a route from current location 710 to destination 720. For example, route 730 is the shortest route connecting roads where vehicle 600 can travel in the shortest duration to destination 720.

In the present embodiment, an identification number (e.g., A001, etc.) is assigned to each of a plurality of roads. As illustrated in FIG. 36, the identification number(s) of one or more roads included in route 730 is/are associated with detailed information 740 on the road(s) in the route information.

Detailed information 740 is information on the details of route 730. Specifically, detailed information 740 indicates a road included in route 730 and the condition of that road. For example, as illustrated in FIG. 36, detailed information 740 includes information on whether autonomous driving is allowed on the corresponding road, the number of streetlights (i.e., the brightness on the road at night), the traffic volume, and other annexed information. In addition, as illustrated in FIG. 37, detailed information 740 may include the distance along route 730 and the time it takes to cover route 730.

In the present embodiment, route information acquirer 422 acquires current location 710 included in the route information with a location-finding system, such as the GPS. Cooperating with the car navigation system, route information acquirer 422 acquires destination 720 input by driver 601 and route 730 determined based on destination 720. Route information acquirer 422 may acquire current location 710 by having driver 601 input current location 710.

Route information acquirer 422 acquires detailed information 740 by inquiring of a road management center or the like based on acquired route 730. Specifically, route information acquirer 422 acquires information on whether autonomous driving is allowed, the number of streetlights, the traffic volume, and so on.

Although route information acquirer 422 acquires route information by receiving a setting of destination 720 from driver 601 with use of the car navigation system in the present embodiment, this is not a limiting example. For example, route information acquirer 422 may acquire route information based only on current location 710. For example, when a traveling route is set for at least a predetermined distance, such as on an expressway (e.g., from a current location to the nearest exit), route information acquirer 422 can acquire route information based only on current location 710.

Alternatively, route information acquirer 422 may acquire route information based on a traveling history or the like of vehicle 600. For example, when vehicle 600 is used for a commute, it is possible to presume that vehicle 600 travels the same route at substantially the same time every day.

[4-1-3. Sleepiness Estimator]

Sleepiness estimator 430 estimates the sleepiness of driver 601 based on biometric information and route information. Specifically, sleepiness estimator 430 estimates the current sleepiness based on biometric information and estimates the future sleepiness based on the estimated sleepiness and route information. To be more specific, sleepiness estimator 430 estimates the sleepiness on route 730.

For example, sleepiness estimator 430 can estimate the time it takes to reach a predetermined location on route 730 based on the distance along route 730 and the time it takes to cover route 730 included in route information, and thus sleepiness estimator 430 can estimate the sleepiness to be held at the predetermined location. In addition, sleepiness estimator 430 corrects the estimated sleepiness in accordance with the condition of a road at a predetermined location. For example, when the predetermined location is in a school zone or in an accident-prone area, sleepiness estimator 430 raises the estimated sleepiness level. This makes it possible to induce wakefulness in driver 601 so as to have the sleepiness level of driver 601 reduced at a timing at which vehicle 600 passes through a school zone or the like (in reality, at a timing prior to when vehicle 600 passes therethrough).

In the present embodiment, as illustrated in FIG. 35, sleepiness estimator 430 includes determiner 132, predictor 133, and sleepiness causing degree determiner 434. Determiner 132 and predictor 133 are similar to those illustrated in Embodiments 1 to 3, and thus descriptions thereof will be omitted.

Sleepiness causing degree determiner 434 determines the sleepiness causing degree based on route information. Specifically, sleepiness causing degree determiner 434 determines the sleepiness causing degree based on the correspondence relationship illustrated in FIG. 38. FIG. 38 illustrates an example of a relationship between auxiliary information (route information) and the sleepiness causing degree (how likely a person becomes sleepy) or the intensity of a waking stimulus.

For example, a long distance along route 730 leads to a long driving time, and driver 601 is more likely to become sleepy. In contrast, a short distance along route 730 can keep the driving time short, and thus driver 601 is less likely to become sleepy. Therefore, sleepiness causing degree determiner 434 raises the sleepiness causing degree when the distance along route 730 is long or when the driving time is long and lowers the sleepiness causing degree when the distance along route 730 is short or when the driving time is short.

For example, when the traffic volume on route 730 is heavy, a traffic congestion is more likely to occur, and driver 601 is more likely to become sleepy. In contrast, when the traffic volume on route 730 is light, a traffic congestion is less likely to occur, and driver 601 is less likely to become sleepy. Therefore, sleepiness causing degree determiner 434 raises the sleepiness causing degree when the traffic volume on route 730 is heavy and lowers the sleepiness causing degree when the traffic volume on route 730 is light.

For example, when route 730 is dark, such as when there are a small number of streetlights on route 730, there is not much light stimulus, and driver 601 is more likely to become sleepy. In contrast, when route 730 is bright, such as when there are a large number of streetlights on route 730, there is a strong light stimulus, and driver 601 is less likely to become sleepy. Therefore, sleepiness causing degree determiner 434 raises the sleepiness causing degree when route 730 is dark and lowers the sleepiness causing degree when route 730 is bright.

For example, route 730 may include a section where autonomous driving is allowed. During autonomous driving, driver 601 does not need to focus on driving, can relax, and is more likely to become sleepy. However, it is not necessary to induce wakefulness in driver 601 in this case, and it is rather desirable to create an environment where driver 601 will be able to focus on driving after the end of the autonomous driving.

Therefore, sleepiness causing degree determiner 434 lowers the sleepiness causing degree immediately after the start of autonomous driving. This makes it possible to increase a relaxation effect on driver 601 by reducing a waking stimulus given to driver 601 or by refraining from giving any waking stimulus to driver 601. Wakefulness inducer 310 may provide a stimulus to induce sleep in driver 601 immediately after the start of autonomous driving.

In contrast, sleepiness causing degree determiner 434 raises or maximizes the sleepiness causing degree immediately before the end of autonomous driving. Thus, wakefulness inducer 310 can give an intense waking stimulus to driver 601 to cause driver 601 to drive in a highly wakeful state.

For example, when route 730 includes a road, such as an accident-prone area or a school zone, where driver 601 is required to drive in a highly wakeful state, sleepiness causing degree determiner 434 raises the sleepiness causing degree. Thus, wakefulness inducer 310 can give an intense waking stimulus to driver 601 to cause driver 601 to drive in a highly wakeful state.

Sleepiness causing degree determiner 434 may estimate a road where vehicle 600 will be driving at a predetermined timing (second point in time) in the future and determine the sleepiness causing degree on the estimated road based on detailed information 740. For example, sleepiness causing degree determiner 434 estimates a road where vehicle 600 is expected to travel every predetermined period and determines the sleepiness causing degree on the estimated road every predetermined period based on detailed information 740. This makes it possible to periodically predict the sleepiness of driving driver 601 with high accuracy and to effectively induce wakefulness in driver 601.

Alternatively, sleepiness causing degree determiner 434 may determine the sleepiness causing degree for each road. Specifically, sleepiness causing degree determiner 434 determines the sleepiness causing degree on each of roads A004, B003, A001, B001, and A002 indicated in FIG. 36. Thus, predictor 133 can estimate the sleepiness of driver 601 held while vehicle 600 is traveling on each road with high accuracy, and wakefulness can be induced effectively in driver 601.

In the present embodiment, sleepiness causing degree determiner 434 may determine the sleepiness causing degree based not only on route information but also on information on a past activity of driver 601 (referred to below as past activity information). The past activity information corresponds to the five-sense information that driver 601 has perceived at a past point in time. In other words, in the present embodiment, five-sense information acquirer 221 acquires past activity information.

For example, past activity information includes the hours of sleep that driver 601 had the day before driving, the time when driver 601 had coffee before driving (i.e., the time when driver 601 consumed caffeine), and the time when driver 601 had a meal before driving. For example, five-sense information acquirer 221 estimates the hours of sleep that driver 601 had the day before based on on/off history information of an illumination device in a bedroom of driver 601. In addition, five-sense information acquirer 221 estimates the time when driver 601 had coffee or a meal based on a thermal image obtained from a thermal image sensor provided in an air conditioner in a dining room of driver 601, a visible light image obtained from an in-room camera provided in a television set or the like, use history information of a microwave oven, open/close history information of a refrigerator, or the like.

For example, sleepiness causing degree determiner 434 raises the sleepiness causing degree of driver 601 when the hours of sleep that driver 601 had the day before is short and driver 601 did not get enough sleep and lowers the sleepiness causing degree of driver 601 when driver 601 had enough hours of sleep. For example, sleepiness causing degree determiner 434 lowers the sleepiness causing degree of driver 601 when driver 601 has had coffee immediately before driving.

For example, sleepiness causing degree determiner 434 raises the sleepiness causing degree of driver 601 when driver 601 has had a large meal immediately before driving.

In this manner, in the present embodiment, sleepiness causing degree determiner 434 determines the sleepiness causing degree based on route information or based on route information and past activity information. As in Embodiments 1 to 3, sleepiness causing degree determiner 434 may determine the sleepiness causing degree based on other information, such as five-sense information or emotion information.

[4-1-4. Receiver]

Receiver 520 receives an instruction on the intensity of a waking stimulus from the outside. For example, receiver 520 is implemented by a user interface device, such as a touch panel, and receives an instruction from driver 601.

In the present embodiment, receiver 520 receives a range specification on the intensity of a waking stimulus from driver 601. The range specification received by receiver 520 is output to wakefulness inducer 310. Wakefulness inducer 310 so induces wakefulness in driver 601 as to keep the sleepiness level of driver 601 low with a stimulus within the range received by receiver 520.

This makes it possible to keep driver 601 from receiving an excessively intense waking stimulus or the like and to assist driver 601 in driving comfortably.

Receiver 520 may receive physical condition information from driver 601. For example, receiver 520 may have driver 601 input his/her self-diagnosis result on whether driver 601 has seen a doctor or whether driver 601 is suffering from a slight cold. The acquired physical condition information is output to wakefulness inducer 310. Physical condition information may be acquired not from receiver 520 but from a clinic or the like as a doctor's diagnosis result.

Wakefulness inducer 310 may determine a means for inducing wakefulness in driver 601 in accordance with the physical condition of driver 601. For example, when the physical condition of driver 601 is bad, wakefulness inducer 310 induces wakefulness in driver 601 with use of not air conditioning or the like but a means that has a smaller influence on the physical condition, such as illumination or a sound.

[4-2. Operation]

Now, with reference to FIGS. 39 and 40, an operation of sleepiness estimating device 400 and an operation of wakefulness inducing device 500 according to the present embodiment will be described.

Figure 39:
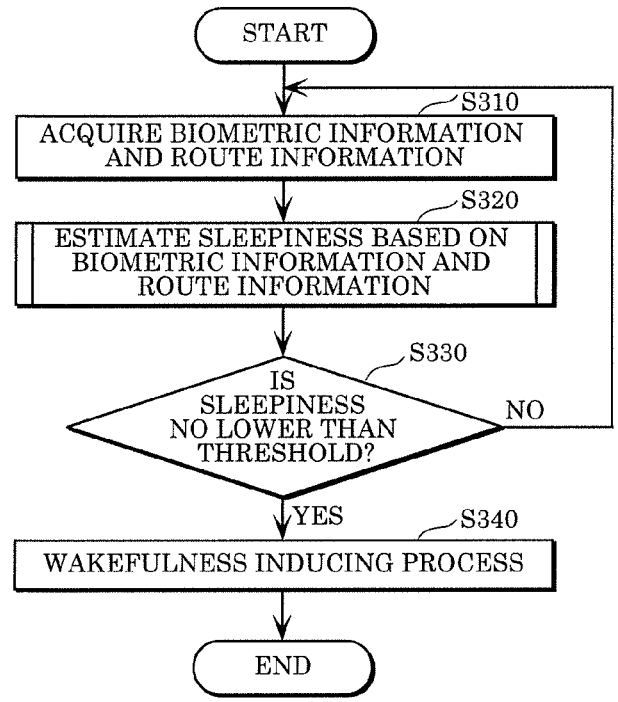
FIG. 39 is a flowchart illustrating an operation of a wakefulness inducing device according to Embodiment 4.

FIG. 39 is a flowchart illustrating an operation of wakefulness inducing device 500 according to the present embodiment. FIG. 40 is a flowchart illustrating an operation of sleepiness estimating device 400 according to the present embodiment.

As illustrated in FIG. 39, first, sleepiness estimating device 400 acquires biometric information and route information (S310). Specifically, biometric information acquirer 110 acquires biometric information, and route information acquirer 422 of auxiliary information acquirer 420 acquires route information. At this point, five-sense information acquirer 221 may acquire past activity information, visual information, and so on.

Next, sleepiness estimator 430 estimates the sleepiness of driver 601 based on the biometric information and the route information (S320). Details of the process of estimating the sleepiness will be described below with reference to FIG. 40.

Figure 40:
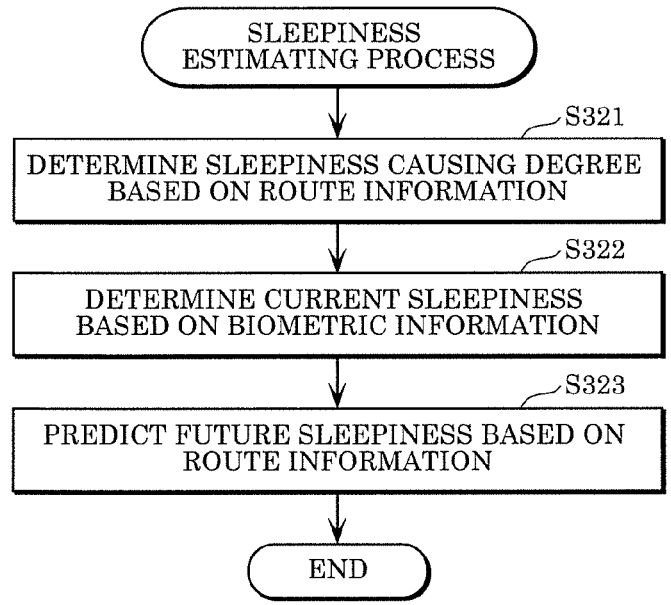
FIG. 40 is a flowchart illustrating an operation of the sleepiness estimating device according to Embodiment 4.

As illustrated in FIG. 40, in the process of estimating the sleepiness, first, sleepiness causing degree determiner 434 determines the sleepiness causing degree (how likely a person becomes sleepy) based on the route information (S321). Specifically, sleepiness causing degree determiner 434 determines the sleepiness causing degree based on the correspondence relationship between route information and the sleepiness causing degree illustrated in FIG. 38. For example, sleepiness causing degree determiner 434 determines the sleepiness causing degree for each road included in the route information.

Next, determiner 132 determines the current sleepiness based on the biometric information (S322). Specifically, determiner 132 determines the current sleepiness based on the correspondence relationship between the frequency of blinking and the sleepiness level illustrated in FIG. 8.

Next, predictor 133 predicts the future sleepiness based on the current sleepiness and the sleepiness causing degree (S323). Specifically, predictor 133 changes the sleepiness level determined by determiner 132 in accordance with the sleepiness causing degree determined by sleepiness causing degree determiner 434. When the sleepiness causing degree is determined for each predetermined period or for each road, predictor 133 can predict the sleepiness of driving driver 601 held at a predetermined timing or the sleepiness held while driver 601 is traveling on a predetermined road.

Referring back to FIG. 39, when the estimated sleepiness level is no lower than a threshold (YES in S330), wakefulness inducer 310 performs a wakefulness inducing process for driver 601 (S340). In the present embodiment, wakefulness inducer 310 induces wakefulness in driver 601 by controlling at least one of illumination device 611, speaker 612, air-conditioning device 613, or scent-emitting device 614 provided in vehicle 600.

For example, in order to induce wakefulness in driver 601, wakefulness inducer 310 increases the intensity of light emitted from illumination device 611. Alternatively, wakefulness inducer 310 may raise the sound output from speaker 612. Alternatively, wakefulness inducer 310 may intensify the airflow blown out from air-conditioning device 613 and blow the air toward driver 601. Alternatively, wakefulness inducer 310 may cause scent-emitting device 614 to emit a highly irritant odor.

At this point, for example, auxiliary information acquirer 420 may acquire environmental information on an environment inside vehicle 600. For example, the environmental information includes at least one of the heat discharge, the illuminance, the carbon dioxide ($CO_2$) concentration, the oxygen ($O_2$) concentration, the wind speed, or the like. Wakefulness inducer 310 induces wakefulness in driver 601 with a suitable means based on the environmental information.

When the amount of remaining fuel, such as gasoline or electric power, is low on long route 730, wakefulness inducer 310 may adjust a waking stimulus to be given to driver 601 so that vehicle 600 will not run out of fuel before reaching destination 720. In other words, the route information may be used to control the energy in vehicle 600.

[4-3. Recapitulation]

When the current sleepiness is estimated based on the biometric information of driver 601 and the sleepiness level of driver 601 is high, it is conceivable to induce wakefulness in driver 601. In this case, however, the sleepiness level of driver 601 is already high, his/her attentiveness is low, and driver 601 is not in a condition suited for driving. Therefore, even if wakefulness is induced after the sleepiness level has been determined to be high, it takes some time for driver 601 to become wakeful, and the condition that is not suited for driving may continue.

In this respect, sleepiness estimating device 400 and wakefulness inducing device 500 according to the present embodiment include route information acquirer 422 that acquires route information and estimate the future sleepiness of driver 601 based on the acquired route information.

Since wakefulness inducing device 500 according to the present embodiment can estimate the future sleepiness of driver 601 with high accuracy, driver 601 can be made wakeful before the attentiveness decreases along with a rise in the sleepiness level of driver 601. In other words, wakefulness inducing device 500 can suppress, in advance, a rise in the sleepiness level of driver 601.

In particular, sleepiness estimating device 400 according to the present embodiment estimates the sleepiness of driver 601 based on route information indicating route 730 where vehicle 600 driven by driver 601 is planning to travel. Therefore, wakefulness inducing device 500 can give an appropriate waking stimulus to driver 601 in accordance with the road condition of route 730.

Although an example in which the sleepiness causing degree is determined based on route information has been illustrated in the present embodiment, this is not a limiting example. For example, the intensity of a waking stimulus may be determined based on route information. For example, when a highly wakeful state is required, such as immediately before the end of autonomous driving or in an accident-prone area or a school zone, wakefulness inducer 310 may give a strong waking stimulus to driver 601 regardless of the sleepiness level of driver 601 or regardless of how likely driver 601 may become sleepy.

Other Embodiments

Thus far, a sleepiness estimating device according to one or more aspects has been described based on some embodiments, but the present disclosure is not limited by these embodiments. Unless departing from the spirit of the present disclosure, an embodiment obtained by making various modifications conceivable by a person skilled in the art to the present embodiments and an embodiment obtained by combining components of different embodiments are encompassed by the scope of the present disclosure.

For example, when there are a plurality of users, a sleepiness estimating device may estimate the sleepiness of each user.

With regard to the taste, the use of meal history information has been described, but this is not limited to the taste. History information for each piece of five-sense information may be used for the sight, the hearing, the sense of smell, or the sense of touch. For example, history information indicating the browsing history of the content that a user has been browsing in the past five minutes may be used as visual information. The browsing history is not limited to the browsing history within the past five minutes, and the browsing history of the content that a user has been browsing from a much earlier time may be used, and there is no limitation on how far back the browsing history can go. In addition, history information of music to which a user has been listening may be used as auxiliary information. In this manner, history information to be used is not limited to meal history information, and history information on other pieces of five-sense information may also be used.

There is no particular limitation on how the devices described in the foregoing embodiments communicate with each other. When the devices are to communicate wirelessly, systems for wireless communication (communication standards) include, for example, near-field wireless communication, such as Zigbee (registered trademark), Bluetooth (registered trademark), or a wireless local area network (LAN). Alternatively, systems for wireless communication (communication standards) may include communication via a wide-area communication network, such as the internet. The devices may communicate through wired communication, instead of wireless communication. Specifically, wired communication includes communication that uses power line communication (PLC) or a wired LAN.

In the foregoing embodiments, a process executed by a specific processor may be executed by another processor. In addition, the order of a plurality of processes may be changed, or a plurality of processes may be executed in parallel. How the components included in a sleepiness estimating device are distributed to a plurality of devices is merely an example. For example, a component included in one device may be included instead in another device. A sleepiness estimating device may be implemented in a single device.

For example, the processes described in the foregoing embodiments may be implemented through centralized processing with a single device (system) or through distributed processing among a plurality of devices. The above-described program may be executed by a single processor or by a plurality of processors. In other words, either one of centralized processing and distributed processing may be employed.

In the foregoing embodiments, a part of the whole of the components, such as a controller, may be implemented by dedicated hardware or implemented as a software program suitable for each component is executed. The components may each be implemented as a program executer, such as a central processing unit (CPU) or a processor, reads out a software program recorded in a recording medium, such as a hard disk drive (HDD) or a semiconductor memory, and executes the software program.

The components, such as a controller, may be implemented by one or more electronic circuits. The one or more electronic circuits may each be a general-purpose circuit or a dedicated circuit.

The one or more electronic circuits may include a semiconductor device, an integrated circuit (IC), or a large-scale integration (LSI), for example. An IC or an LSI may be integrated in a single chip or in a plurality of chips. Although the name used herein is IC or LSI, a circuit may also be called a system LSI, a very large-scale integration (VLSI), or an ultra large-scale integration (ULSI) depending on the degree of integration. A field-programmable gate array (FPGA) that can be programmed after manufacturing an LSI can also be used for the same purpose.

General or specific aspects of the present invention may be implemented in the form of a system, an apparatus, a method, an integrated circuit, or a computer program. Alternatively, the general and specific aspects may be implemented in the form of a computer-readable non-transitory recording medium, such as an optical disc, an HDD, or a semiconductor memory, storing the computer program. Furthermore, the general or specific aspects may be implemented through a desired combination of a system, an apparatus, a method, an integrated circuit, a computer program, and a recording medium.

In the foregoing embodiments, various changes, substitutions, additions, omissions, and so on can be made within the scope of the claims and equivalents thereof.

INDUSTRIAL APPLICABILITY

The present disclosure can be used as a sleepiness estimating device that can estimate the sleepiness with high accuracy. The present disclosure can be used to manage a person and assist a person in being wakeful in various environments, including an office, an after-school learning center, and a vehicle, for example.

The invention claimed is:
1. A sleepiness estimating device, comprising:
a biometric information acquirer that acquires biometric information of a person;
an auxiliary information acquirer that acquires auxiliary information including at least one of five-sense information perceived by the person or emotion information indicating an emotion of the person; and
a sleepiness estimator that estimates a sleepiness of the person based on the biometric information and the auxiliary information.

2. The sleepiness estimating device according to claim 1, wherein
the sleepiness estimator includes:
a corrector that corrects the biometric information based on the auxiliary information; and
a determiner that determines the sleepiness of the person based on the biometric information corrected by the corrector.

3. The sleepiness estimating device according to claim 1, wherein
the sleepiness estimator includes:
a determiner that determines the sleepiness of the person at a first point in time based on the biometric information; and
a predictor that predicts the sleepiness of the person at a second point in time that is after the first point in time, based on the auxiliary information and the sleepiness determined by the deter miner.

4. The sleepiness estimating device according to claim 1, wherein
the five-sense information includes visual information on a stimulus for sight of the person.

5. The sleepiness estimating device according to claim 4, wherein
the auxiliary information acquirer acquires, as the visual information, a content of a displayed material at which the person is looking.

6. The sleepiness estimating device according to claim 5, wherein
the sleepiness estimator
includes a learner that learns a preference of the person regarding the displayed material, and
estimates the sleepiness of the person based further on a learning result of the learner.

7. The sleepiness estimating device according to claim 5, wherein
the sleepiness estimator estimates the sleepiness of the person based further on a manner of operation performed by the person on the displayed material.

8. The sleepiness estimating device according to claim 1, wherein
the five-sense information includes auditory information on a stimulus for hearing of the person.

9. The sleepiness estimating device according to claim 8, wherein
the auxiliary information acquirer acquires, as the auditory information, audio information of surroundings of the person.

10. The sleepiness estimating device according to claim 1, wherein
the five-sense information includes olfactory information on a stimulus for a sense of smell of the person.

11. The sleepiness estimating device according to claim 1, wherein
the five-sense information includes taste information on a stimulus for taste of the person.

12. The sleepiness estimating device according to claim 11, wherein
the auxiliary information acquirer acquires, as the taste information, meal history information of the person.

13. The sleepiness estimating device according to claim 12, wherein
the auxiliary information acquirer acquires, as the taste information, information indicating food that the person is eating.

14. The sleepiness estimating device according to claim 1, wherein
the five-sense information includes touch information on a stimulus for a sense of touch of the person.

15. The sleepiness estimating device according to claim 14, wherein
the auxiliary information acquirer acquires, as the touch information, a frequency at which the sense of touch of the person is stimulated.

16. The sleepiness estimating device according to claim 14, wherein
the auxiliary information acquirer acquires, as the touch information, information on a chair on which the person is sitting.

17. The sleepiness estimating device according to claim 1, wherein
the biometric information acquirer acquires, as the biometric information, information on blinking of the person.

18. A wakefulness inducing device, comprising:
the sleepiness estimating device according to claim 1; and
a wakefulness inducer that induces wakefulness in the person based on the sleepiness estimated by the sleepiness estimator.

19. The wakefulness inducing device according to claim 18, wherein
the wakefulness inducer changes an image displayed on a display of an electronic device operated by the person.

20. The wakefulness inducing device according to claim 18, wherein
the wakefulness inducer communicates information on the sleepiness of the person.

* * * * *